United States Patent
Silva et al.

(10) Patent No.: US 10,939,943 B2
(45) Date of Patent: Mar. 9, 2021

(54) ORTHOPEDIC BONE PLATE SYSTEM

(71) Applicant: OsteoCertus, LLC, Pembroke Pines, FL (US)

(72) Inventors: Cesar Silva, Pembroke Pines, FL (US); David Augusto Silva, Popayán (CO); Javier E. Castaneda, Miami, FL (US)

(73) Assignee: OsteoCertus, LLC, Pembroke Pines, FL (US)

( * ) Notice: Subject to any disclaimer, the term of this patent is extended or adjusted under 35 U.S.C. 154(b) by 437 days.

(21) Appl. No.: 15/826,651

(22) Filed: Nov. 29, 2017

(65) Prior Publication Data

US 2018/0140339 A1 May 24, 2018

Related U.S. Application Data

(63) Continuation-in-part of application No. 15/335,162, filed on Oct. 26, 2016, now Pat. No. 10,478,237, which is a continuation-in-part of application No. 14/987,425, filed on Jan. 4, 2016, now Pat. No. 10,258,402.

(51) Int. Cl.
  *A61B 17/88* (2006.01)
  *A61B 17/80* (2006.01)
  *A61B 17/86* (2006.01)

(52) U.S. Cl.
  CPC ...... *A61B 17/8085* (2013.01); *A61B 17/8057* (2013.01); *A61B 17/865* (2013.01); *A61B 17/888* (2013.01); *A61B 17/8863* (2013.01); *A61B 17/8605* (2013.01)

(58) Field of Classification Search
  CPC . A61B 17/80; A61B 17/8057; A61B 17/8085; A61B 17/8863; A61B 17/888; A61B 17/1728
  See application file for complete search history.

(56) References Cited

U.S. PATENT DOCUMENTS

| | | |
|---|---|---|
| 5,002,544 A | 3/1991 | Klaue et al. |
| 5,053,036 A | 10/1991 | Perren et al. |
| 5,151,103 A | 9/1992 | Tepic et al. |
| 5,564,302 A | 10/1996 | Watrous |
| 5,690,631 A | 11/1997 | Duncan et al. |
| 6,001,099 A | 12/1999 | Huebner |
| 6,004,353 A | 12/1999 | Masini |

(Continued)

FOREIGN PATENT DOCUMENTS

| KR | 101201603 B1 | 10/2011 |
|---|---|---|
| WO | WO2014/074850 A1 | 5/2014 |

OTHER PUBLICATIONS 1.5 mm LCP Modular Mini Fragment System. 1.5 mm instrument and implant modules. Technique Guide, Synthes, 2009.

(Continued)

*Primary Examiner* — Si Ming Ku
(74) *Attorney, Agent, or Firm* — Gordon & Jacobson, P.C.

(57) ABSTRACT

A bone plate has first and second sides, each with the same structure. The plate includes nodes separated by deformable bridges. Each node defines a screw hole, and wings extending laterally therefrom. The wings taper in thickness between the first and second sides. Screw holes are threaded into the nodes. The plate can be shaped to the bone by deformation at the bridges or removal of portions of the plate at bridges.

21 Claims, 27 Drawing Sheets

(56) References Cited

U.S. PATENT DOCUMENTS

| | | |
|---|---|---|
| 6,309,393 B1 | 10/2001 | Tepic et al. |
| 6,348,052 B1 | 2/2002 | Sammarco |
| 6,454,770 B1 | 9/2002 | Klaue |
| 7,189,237 B2 | 3/2007 | Huebner |
| 7,704,251 B2 | 4/2010 | Huebner et al. |
| 7,740,634 B2 | 6/2010 | Orbay et al. |
| 7,771,433 B2 | 8/2010 | Orbay et al. |
| 7,935,126 B2 * | 5/2011 | Orbay ............... A61B 17/80 606/101 |
| 8,080,010 B2 | 12/2011 | Schulz et al. |
| 8,167,918 B2 | 5/2012 | Strnad et al. |
| 8,172,886 B2 | 5/2012 | Castaneda et al. |
| 8,231,663 B2 | 7/2012 | Kay et al. |
| 8,292,898 B2 | 10/2012 | Castaneda et al. |
| 8,419,745 B2 | 4/2013 | Sixto, Jr. et al. |
| 8,518,088 B2 | 8/2013 | Castaneda et al. |
| 8,568,462 B2 | 10/2013 | Sixto, Jr. et al. |
| 8,632,574 B2 | 1/2014 | Kortenbach et al. |
| 8,702,763 B2 | 4/2014 | Lin et al. |
| 8,992,582 B1 | 3/2015 | Knoepfle et al. |
| 9,918,762 B2 * | 3/2018 | Federspiel ......... A61B 17/8085 |
| 2004/0092935 A1 | 5/2004 | Manderson |
| 2004/0097936 A1 | 5/2004 | Ebid |
| 2005/0149026 A1 | 7/2005 | Butler et al. |
| 2006/0004362 A1 | 1/2006 | Patterson et al. |
| 2006/0095044 A1 * | 5/2006 | Grady, Jr. .......... A61B 17/1728 606/96 |
| 2008/0015591 A1 | 1/2008 | Castaneda et al. |
| 2008/0221574 A1 | 9/2008 | Cavallazzi et al. |
| 2009/0281543 A1 | 11/2009 | Orbay et al. |
| 2009/0299369 A1 | 12/2009 | Orbay et al. |
| 2010/0069966 A1 | 3/2010 | Castaneda et al. |
| 2010/0251861 A1 | 10/2010 | Sixto, Jr. et al. |
| 2011/0022049 A1 | 1/2011 | Huebner et al. |
| 2011/0071572 A1 | 3/2011 | Sixto et al. |
| 2011/0092981 A1 | 4/2011 | Ng et al. |
| 2011/0144698 A1 | 6/2011 | Buchbinder et al. |
| 2012/0065689 A1 | 3/2012 | Prasad et al. |
| 2012/0109214 A1 | 5/2012 | Leither et al. |
| 2013/0023938 A1 | 1/2013 | Huebner et al. |
| 2013/0204307 A1 | 8/2013 | Castaneda et al. |
| 2014/0000092 A1 | 1/2014 | Fritzinger et al. |
| 2014/0243837 A1 * | 8/2014 | Mebarak ................ A61B 17/17 606/96 |

OTHER PUBLICATIONS

Graduated Stability Plates (GSP), Stryker, Leibinger Micro Implant Products, 2004.

Product Rationale & Surgical Technique, ALPS Total Foot System, Biomet Orthopedics, 2012.

* cited by examiner

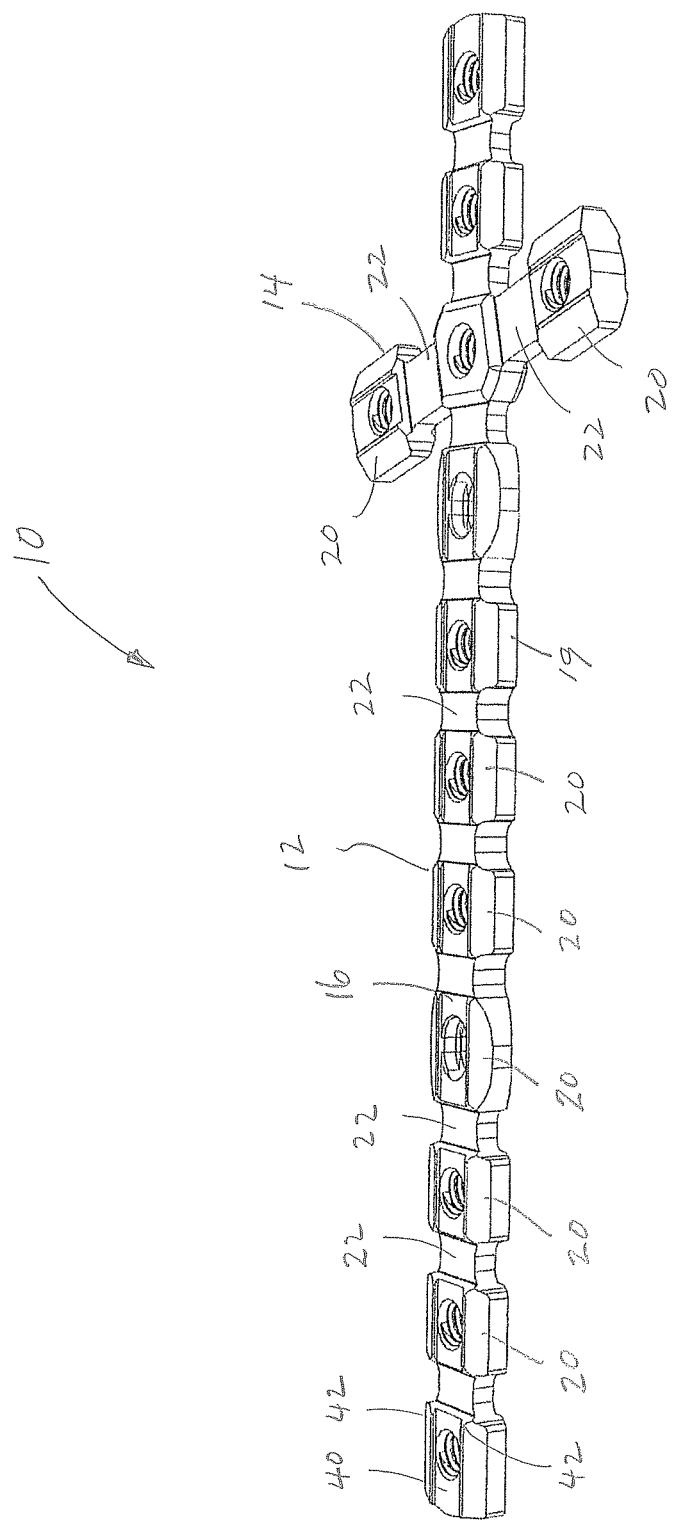

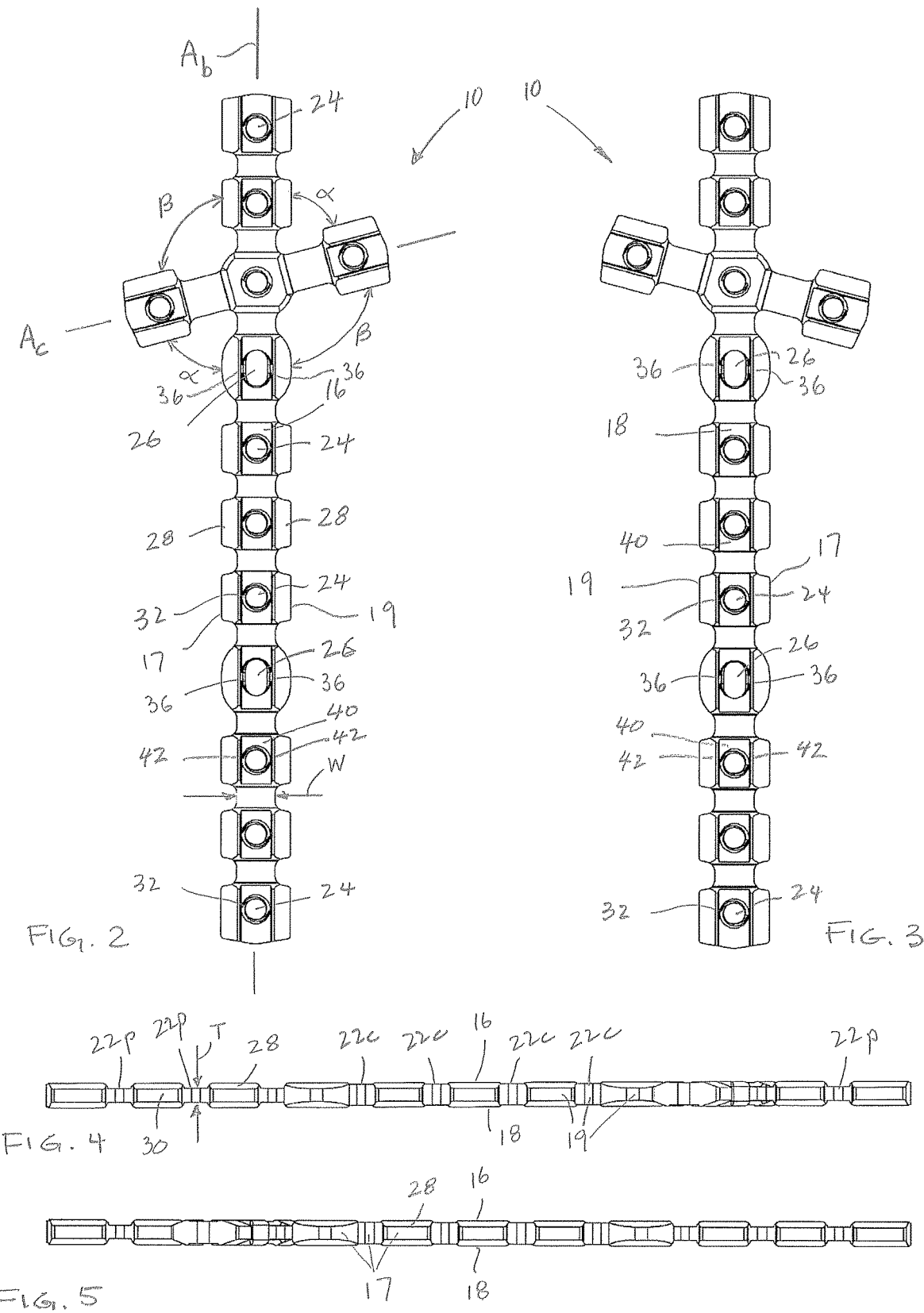

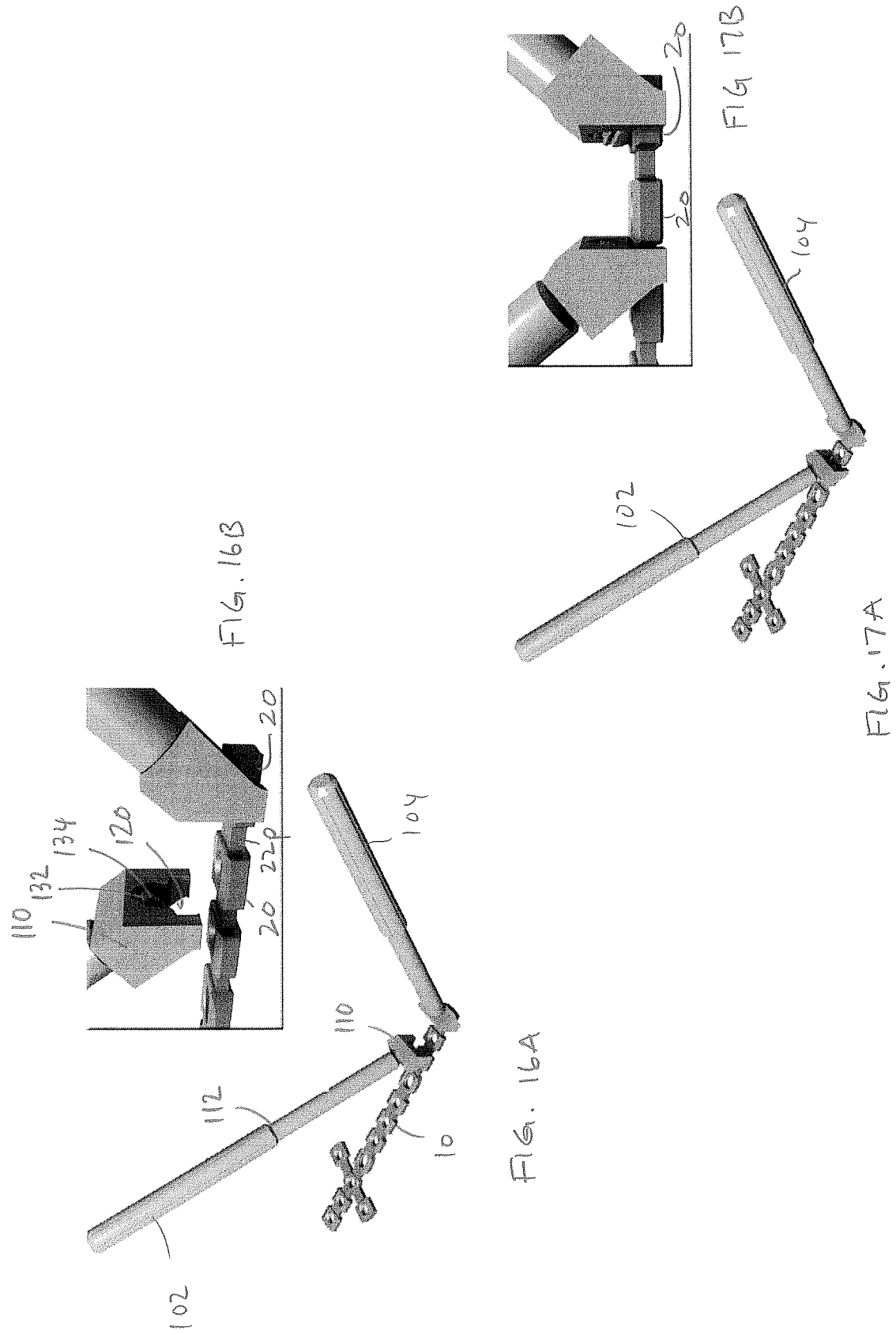

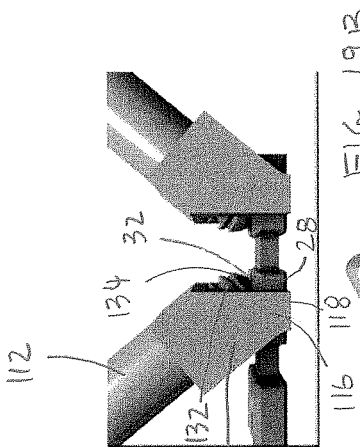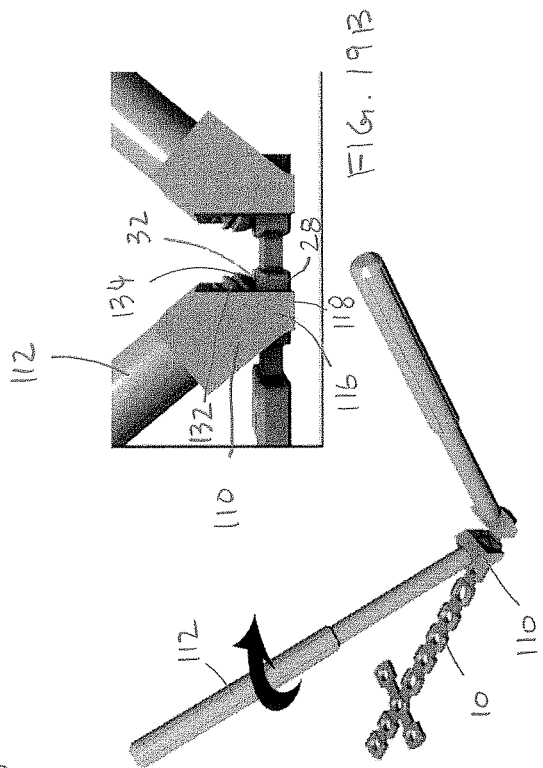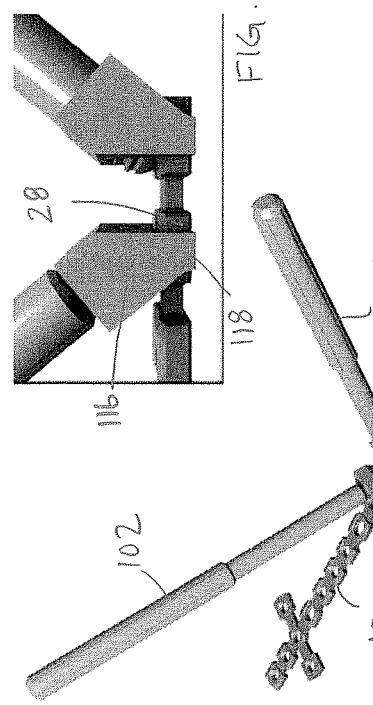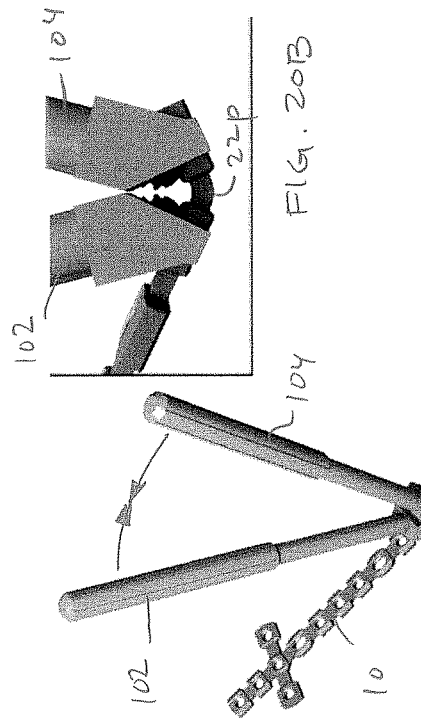

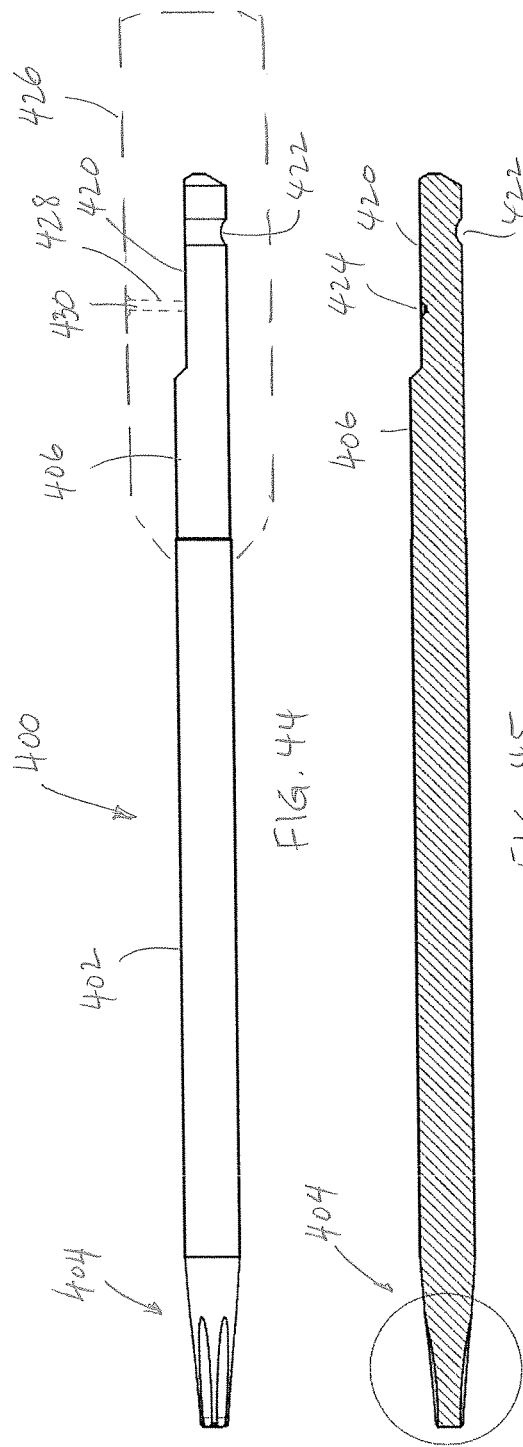
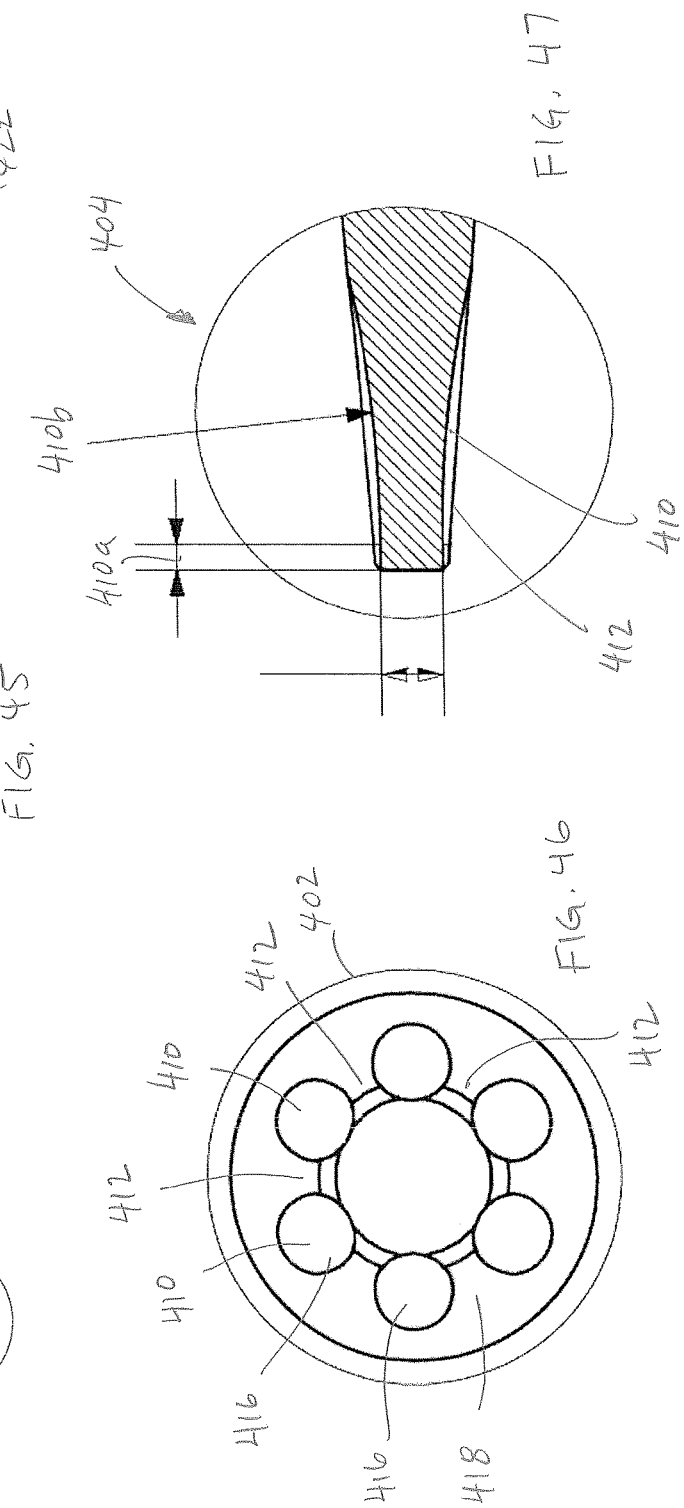

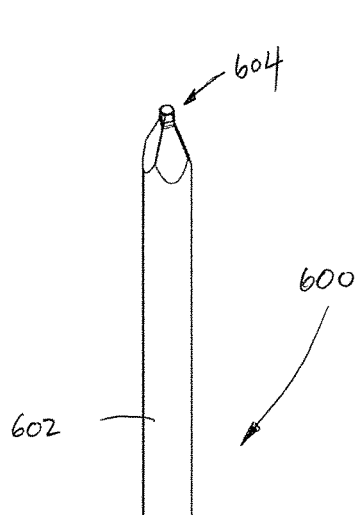
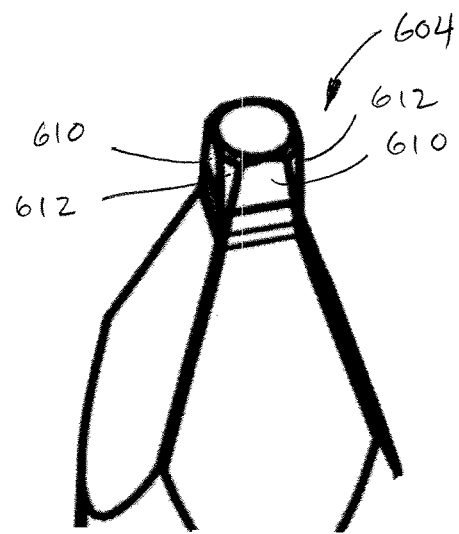
FIG. 52
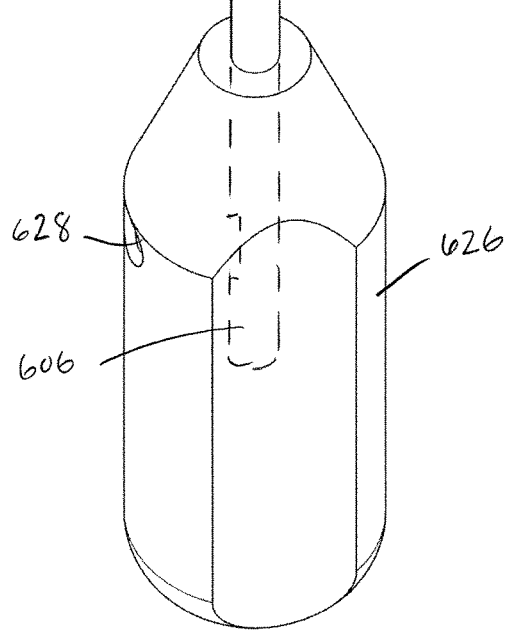
FIG. 51
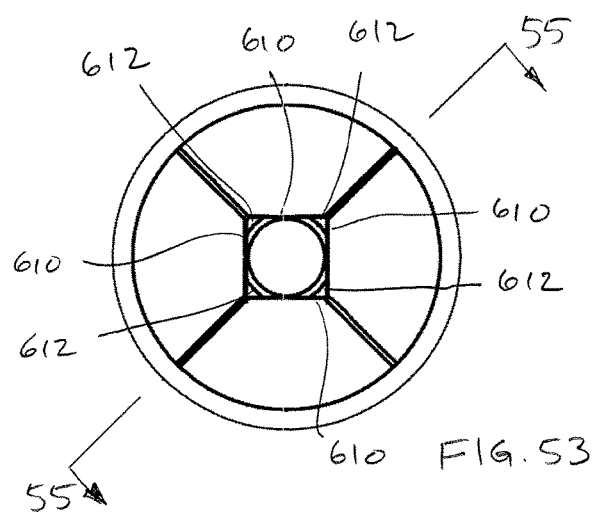
FIG. 53
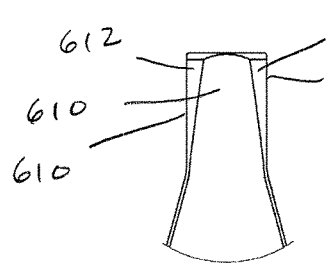
FIG. 54
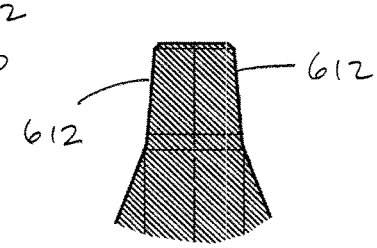
FIG. 55

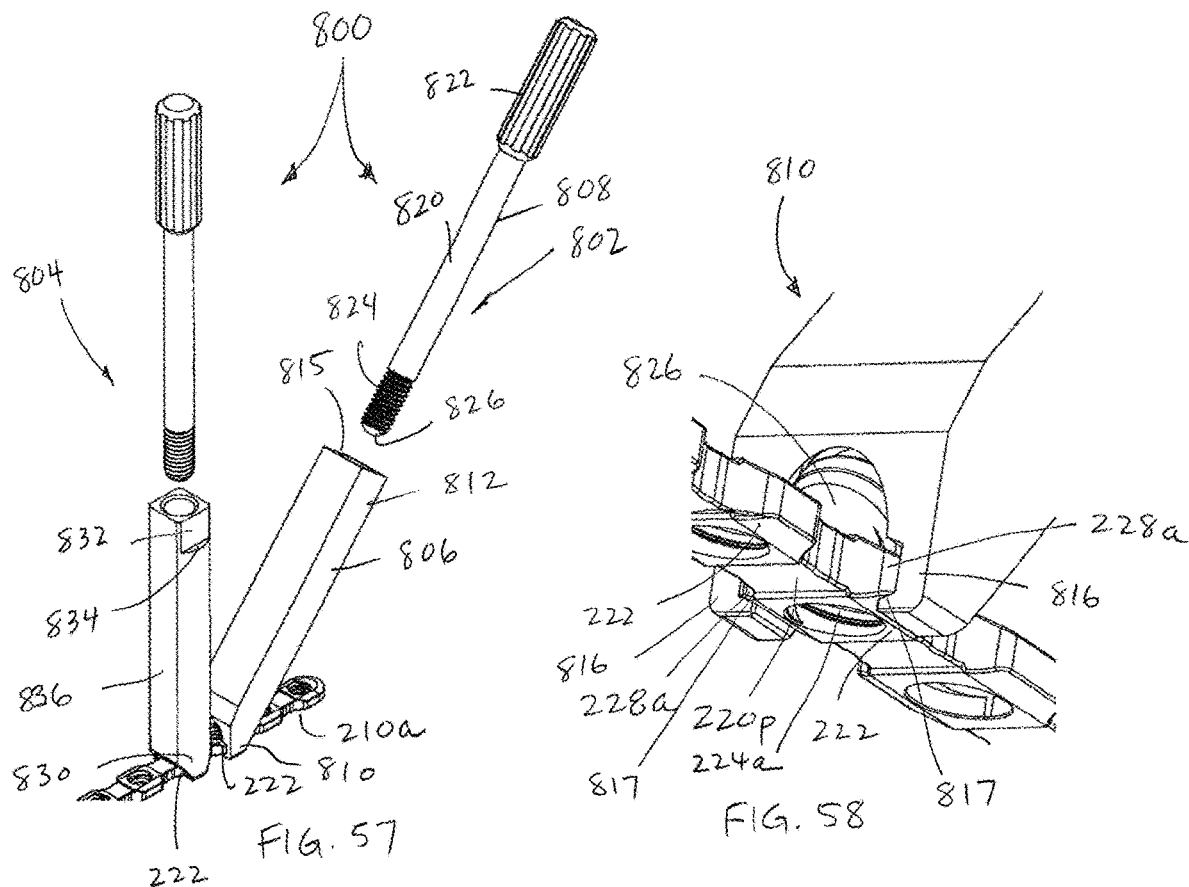
FIG. 57
FIG. 58
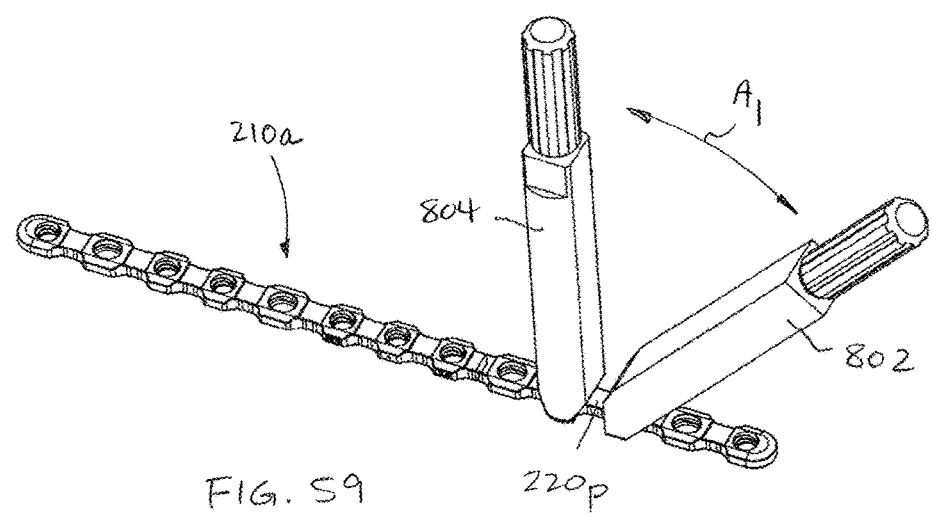
FIG. 59

ORTHOPEDIC BONE PLATE SYSTEM

CROSS-REFERENCE TO RELATED APPLICATIONS

This application is a continuation-in-part of U.S. Ser. No. 15/335,162, filed Oct. 26, 2016, which is a continuation-in-part of U.S. Ser. No. 14/987,425, filed Jan. 4, 2016, both of which are hereby incorporated by reference herein in their entireties.

BACKGROUND

1. Field

The present invention relates to surgery. More particularly, the invention relates to bone plates, instruments, and methods for internal orthopedic fixation in mammals.

2. State of the Art

Orthopedic plates are known for treating traumatic bone injuries in humans and other mammals. With respect to human treatment, significant development has been made in designing plates that are less of a general elongate form, but rather are more particularly adapted to the specific bones for which they are intended. That is, there has been a trend toward developing anatomical plates. In an anatomical plate, the bone-contacting surface of the plate closely fits the surface contours of the bone to which the plate is specifically adapted. These plates are generally provided in two versions of mirrored symmetry for use on the bones of the left and right sides of the body.

While good results have been reported with such anatomical plates, their use requires that treatment centers maintain a large inventory of different plates, each adapted for the different bones of the body, bones of different sizes, and the left and right sides of the body. The maintenance of such an extensive inventory can be costly, which is a significant disadvantage for treatment centers that may use certain plates with only a low frequency.

Further, while for a human population, the expense of a costly inventory often can be justified or required, animal populations do not benefit from such luxury. Veterinary surgical plates are often more basic than their human counterparts, of a general purpose, and not well adapted to the anatomical contours of the bone.

SUMMARY

Sets of two shapes of rigid, metal bone plates are provided in a system. The bone plates of each shape are provided in several sizes and can be adapted for treatment of many different types of bone fractures and bone sizes. The first shape plate is planar, in the form of a 't', and, in an embodiment, consists of a straight body and a cross arm. The second shape plate is planar and straight.

According to an aspect of the first shape bone plate, the cross arm extends transverse to the body at a non-orthogonal angle. The bone plate has a first side and a second side. According to another aspect of the bone plate, each of the first and second sides are adapted with same structure and contours such that each can be positioned against and in contact with the bone being treated, thereby providing treatment for bones on one lateral side of the body when the first side is positioned against the bone, and treatment for bones on the other lateral side of the body when the second side is positioned against a respective bone. As such, the plates have the same structure at their first and second sides.

More particularly, the body and cross arm of each plate include nodes separated by deformable bridges. The body portion defines a body axis extending centrally along the bridges of the body. The cross arm includes a cross axis extending centrally along the bridges of the cross arm. Each node defines a central screw hole, and wings extending laterally outward from the axis on which the node is situated. The wings taper in thickness between the first and second sides. The screw holes in a plurality of the nodes are preferably threaded, and in at least one node is preferably an elongate slot. The threaded screw holes all include an upper countersink.

The body and cross arm further define respective central longitudinal channels on each of the first and second sides of the plate in which the screw holes of the nodes are positioned. The channels have sides defining a pair of rails. When the first side of the plate is placed into contact with the bone, the rails seat against the bone and allow a convex bone to extend into the channels, and the channels at the second side define respective spaces in which screw heads of screws within the screw holes may be recessed. Similarly, when the second side of the plate is placed into contact with the bone, the rails on the second side seat against the bone, and the channels at the first side define respective spaces in which screw heads of screws within the screw holes may be recessed. The nodes at a more central location of the plate are stiffer and more resistant to deformation.

The straight plate in a preferred design has a particular arrangement of thirteen holes. From one end of the plate, the plate has a threaded circular hole, then an oblong hole, then two threaded circular holes, then an oblong hole, then three threaded circular holes, then an oblong hole, then two threaded circular holes, then an oblong hole, and finally a threaded circular hole. The straight second plate defines nodes, wing structures, and channels, as in the cross-arm first plate.

The plates may be shaped by removal of portions of the plate at bridges between the nodes. The removal can be performed with a cutting instrument or by reverse bending until breakage at a selected bridge. Specifically, the straight second plate can be bent towards its longitudinal center to break the plate into two plates: one with six holes and the other with seven holes, and each having threaded circular holes at their respective ends. The plates may be further shaped to the bone by plastic deformation of the plate at the bridges between the nodes.

Selected bridges may include bilateral notches that encourage breakage at a center of a bridge. In addition, selected channels may include raised floors over the screw holes that increase the thickness of the plate thereat to further prevent deformation of the screw holes when shape bending the plate or purposefully breaking the plate.

In accord with another aspect of the system, a bending system is provided to bend the plates at the bridges between the nodes. The bending system includes first and second benders, each of preferably like structure and assembly. Each bender includes a clamp bracket and a handle. The bracket includes a body, an upper threaded hole in the body, and a pair of spaced-apart arms descending from the body, each terminating in a inwardly directed seat. The space between the seats at the lower ends of the arms is sufficient to be received vertically over a bridge of the plate but too small to accommodate vertical passage over the wings of a node. However, the space between the arms in relation to the wings allows the arms to be moved along the axis from a bridge to an adjacent node, with the lower end of the wings of the node engaging the seats. In a first embodiment of a bending system, the handle includes a proximal shaft and a distal threaded clamping bolt which is threadedly coupled within the threaded hole of the bracket and extends into the space between the arms. The end of the clamping bolt is convex and sized to seat against the countersink of a threaded screw hole. The first embodiment of the bending system is adapted to bend the plate out of plane. In a second embodiment of the bending system, the bracket includes lateral exterior slots along an upper portion thereof, and a bending arm is provided that engages within the slots.

In use, an appropriately sized bone plate is selected for a bone, such as a long bone or the pelvis. The orientation of the plate is selected, such that one of the first and second surfaces is identified and/or selected for placement against the bone. The plate is then reshaped as necessary and secured to the bone. The plate may be fully or partially reshaped before any attachment to the bone, or may be preliminarily attached to the bone and then reshaped and further secured.

More particularly, to reshape the plate at a bridge, a pair of benders are positioned on the plate at the two nodes on opposite sides of the bridge. Each bender is placed over a bridge and then slid into place on its respective node. Then the handle is rotated relative to the bracket to cause the clamping bolt to advance against the upper surface of the plate, at the countersink and without entering the threads of the screw hole. When the handle is rotated, the bracket is stably retained on the plate by the position of the arms about the wings of the node. The handle is rotated until the plate is clamped between the clamping bolt and the seats on the arms. Once each bender is coupled to its respective node, a relative force is applied between the benders to deform the bridge and thereby shape the plate.

The system also includes screws for securing the plate to the bone. In a preferred system, both locking screws and compression screws are provided. In addition, screws of different diameter and length are also provided for appropriate fixation and repair of the bone injury.

The system also includes a driver for picking up the screws and driving the screws through the plate and into the bone.

The system provides a limited number of plate designs that accommodate left and right anatomies and which can also be customized in shape via removal of one or more nodes and bending along one or more bridges. The limited plate designs are readily adaptable into treatment even for those surgeons who have not had significant prior experience with anatomical or shapeable plates adapted for specific bones.

The system may be provided in various kits. Each kit includes a plate and a limited number of screws packaged together, e.g., in a tray. The screws include a predefined number of locking screws all of a first length, and a predefined number of non-locking screws all of a second length which is equal to or longer than the first length. The kit preferably also includes one or more plate benders. The kit preferably also includes one or more K-wires that can be used as drill bits and/or fixators. The packaging contains the plate and associated screws, and preferably together with the plate bender and/or the K-wire(s), all separate from other plates and screws.

BRIEF DESCRIPTION OF THE DRAWINGS

FIG. 1 is a perspective view of a plate according to a system described herein.

FIG. 2 is a plan view of a first side of the plate of FIG. 1.
FIG. 3 is a plan view of a second side of the plate of FIG. 1.
FIG. 4 is an elevation view from the right side of the plate as oriented in FIG. 2.
FIG. 5 is an elevation view from the left side of the plate as oriented in FIG. 2.
FIGS. 16A-16B, 17A-17B, 18A-18B, 19A-19B, 20A-20B illustrate methods of bending plates of the system, with the 'A' figures showing the system in total, and the 'B' figures showing enlargements of respective portions in the 'A' figures.
FIG. 44 is a side elevation view of a screwdriver of the system.
FIG. 45 is a longitudinal section view of a shaft of the screwdriver of FIG. 44.
FIG. 46 is an enlarged distal end view of the shaft of the screwdriver of FIG. 44.
FIG. 47 is an enlarged longitudinal section view of the distal end of the shaft of the screwdriver of FIG. 44.
FIG. 51 is a perspective view of another embodiment of a screwdriver for use with the system.

FIG. 52 is an enlarged perspective view of screwdriver of FIG. 51.

FIG. 53 is an enlarged distal end view of the screwdriver of FIG. 51.

FIG. 54 is an enlarged side view of the tip of the screwdriver of FIG. 51.

FIG. 55 is a longitudinal section view across line 55-55 in FIG. 53.

FIG. 57 is a perspective assembly view of another plate bender system in combination with a bone plate.

FIG. 58 is an enlarged bottom perspective view of a portion of the plate bender system of FIG. 57 attached to a bone plate.

FIG. 59 is a top perspective view of the plate bender system of FIG. 57 attached to a bone plate.

DETAILED DESCRIPTION OF THE PREFERRED EMBODIMENTS

Figure 6:
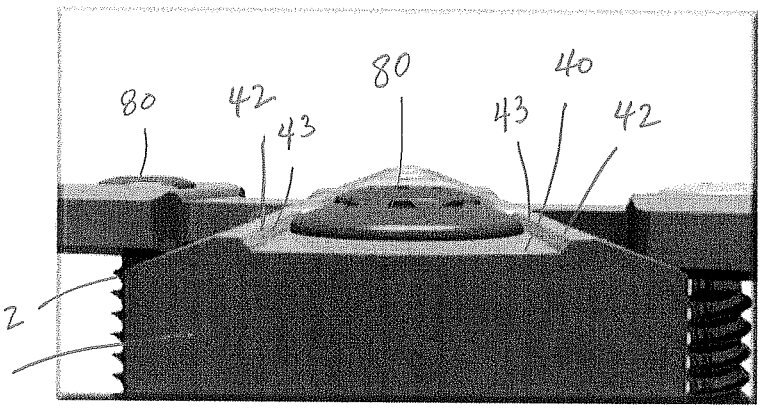
FIG. 6 is a cross sectional perspective view across a body portion of the plate, orthogonal to the longitudinal axis of the body portion.

In accord with the system herein, sets of bone plates of two different shapes are provided. The bone plates of each shape are provided in several sizes and can be adapted for treatment of many different types of bone fractures and bone sizes.

Turning now to FIGS. 1 through 5, a first bone plate 10 is shown. The plate 10 is preferably made of metal, and has sufficient rigidity to provide stability to a broken bone. The bone plate 10 is in the form of a 't' and includes, and in embodiments consists of, a straight body 12 and a straight cross arm 14. The cross arm 14 extends transverse to the body 12 at a non-orthogonal angle, preferably forming two α angles of 75±10°, and two respectively supplementary angles β of 105°±10°, giving the plate a bilaterally asymmetric design.

The bone plate 10 extends in a plane, and has a first side 16, a second side 18, and lateral sides 17, 19 extending between the first and second sides. According to another aspect of the bone plate 10, each of the first and second sides 16, 18 are adapted with the same structure and contours such that each can be positioned against and in contact with the bone being treated, thereby providing treatment for bones on one lateral side of the body when the first side is oriented as a bone contacting surface, and treatment for bones on the other lateral side of the body when the second side is positioned against a respective bone.

More particularly, each of the body 12 and cross arm 14 of the plate 10 includes a linear arrangement of alternating nodes 20 and bridges 22. The body 12 defines a body axis $A_b$ extending centrally along the bridges 22 of the body. The cross arm 14 includes a cross axis $A_c$ extending centrally along the bridges 22 of the cross arm 14. The bridges 22 have a width W extending orthogonal to the respective axis $A_b$, $A_c$ along which it lies, and a thickness T extending between the first and second sides 16, 18. The bridges 22 have a reduced area moment of inertia relative to the nodes 20 such that the bridges have an increased propensity to bending deformation relative to the nodes when a bending force is applied thereto. Also, the bridges 22 have reduced polar moment of inertia relative to the nodes 20 such that the bridges have an increased propensity to twisting deformation relative to the nodes when a torquing force is applied thereto.

Referring back to FIGS. 1 through 5, each node 20 defines a central screw hole 24 or 26, and wings 28 extending laterally outward from the axis on which the node is situated. The wings 28 taper at a common first angle in thickness equally between the first and second sides 16, 18 such that the lateral ends 30 of the wings are thinner than the thickness of the node and are elevated relative to whichever of the first and second sides 16, 18 is the bone contacting surface of the bone plate 10. The screw holes 24, which are provided in a plurality of the nodes, are threaded and include countersinks 32 opening at each of the first and second sides 16, 18; i.e., at each of their ends. The screw holes 26 in two of the relatively longitudinally central nodes of the body 12 are elongate, preferably non-threaded, and define elongate slots. Elongate screw holes 26 include a pair of ledges 36 extending along the sides of the hole that are adapted to functionally either (i) be engaged by the threads on the threaded head of a locking screw and allow locking relative thereto, or (ii) act as a stop for the head of a compression screw. These features are described further below.

The body 12 and cross arm 14 further define respective central longitudinal channels 40 on each of the first and second sides 16, 18 of the plate in which the screw holes 24, 26 of the nodes 20 are positioned. The channels 40 have sides defining a pair of rails 42. When the first side 16 of the plate is made a bone-contacting side, the rails 42 of the first side seat against the bone and allow a convex bone portion to extend at least partially into the channel 40 thereat, and the opposing channel on the second side 18 defines respective spaces on the nodes in which screw heads 80 of screws 82 (FIG. 6) positioned within the screw holes 24 may be recessed. Similarly, when the second side 18 of the plate is placed is made the bone-contacting side and placed into contact with the bone, the rails on the second side seat against the bone, and the channel at the first side defines respective space in which screw heads of screws within the screw holes of the nodes may be recessed. The rails 42 have a beveled medial side 43 extending at an angle.

The bridges $22_c$ at a more central location of the plate 10; i.e., located between the nodes provided with the elongate screw slots 26, are thicker, stiffer and more resistant to deformation, whereas the relatively proximal, distal, and lateral (more peripheral) bridges $22_p$ are thinner and more susceptible to deformation (FIG. 4). The plate 10 may be shaped to the bone by plastic deformation of the plate at the bridges 22 between the nodes 20. More particularly, the thinner bridges $22_p$ are utilized for shaping, as described in more detail below.

Figure 10:
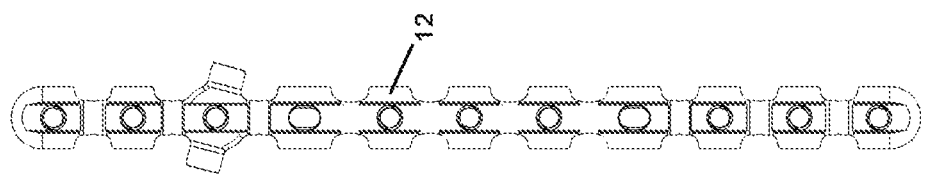
FIGS. 7 through 10 illustrate, in plan view, various exemplar shapes for a plate as shown in FIG. 1, with peripheral portions thereof removed.
Figure 9:
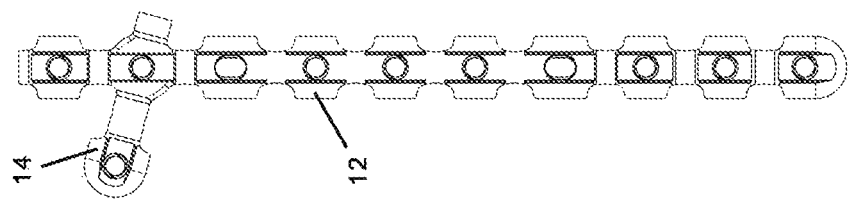
Figure 8:
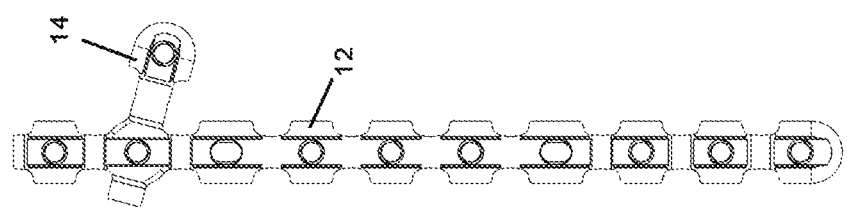
Figure 7:
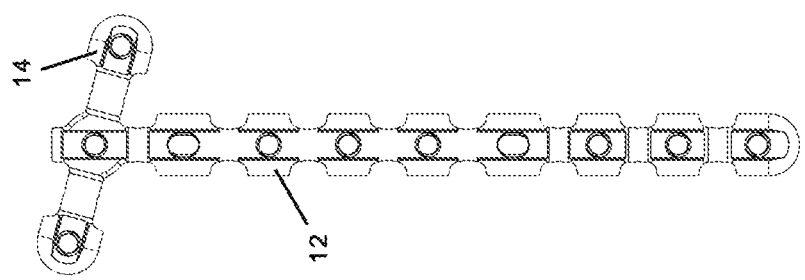

The plate may be further shaped by removal of peripheral portions of the plate at bridges 22 between the nodes. The removal can be performed with a suitable cutting instrument or by reverse bending until breakage at a selected bridge. FIGS. 7 through 10 show various exemplar plate shapes that can be formed by removal of peripheral portions of the plate, preferably about the intersection of the body 12 and cross arm 14. By way of example, the plate can be shaped into a slanted-'T' (FIG. 7), various one-armed shapes (FIGS. 8 and 9), and a straight plate (FIG. 10).

Figure 24:
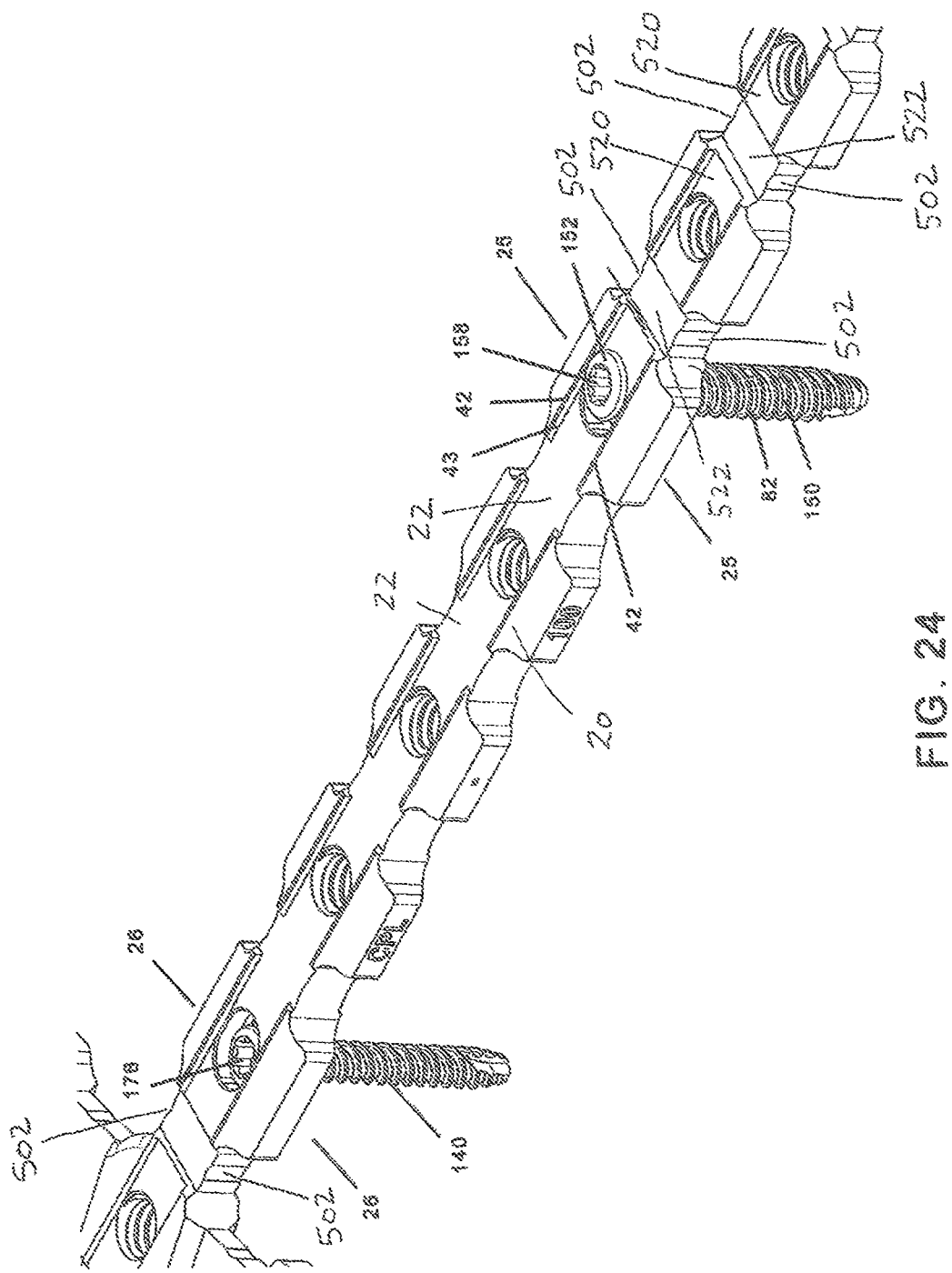
FIG. 24 is a partial perspective view of the bone plate showing a first elongate slot provided with a compression screw and a second elongate slot provided with a locking screw.

Turning to FIG. 24, the bridges 22 may be selectively provided with bilateral notches 502 in the lateral sides 17, 19 that increase the propensity of a bridge 22 to deform and controllably break at a center of the bridge 22 when subject to bending forces. The bridge 22 will break between the surrounding nodes 20 at a centerline defined between two opposed bilateral notches 502. Such notches 502 are preferably located only in zones of the plate at which purposeful plate breakage (separation of the plate into two usable parts, plate shortening, plate reshaping) may be required, typically nearer the ends of the plate, and generally away from the portion of the plate anticipated to overlie the bone fracture zone.

The nodes 20 preferably have a common first plate thickness. The thickness of the bridges is reduced relative to the first plate thickness but not necessarily constant. The bridges generally nearer the end of the plate and also intended to be bent and/or define a break point for the plate, and away from the portion of the plate anticipated to overlie the bone fracture zone have a reduced thickness relative to the bridges which are intended to overlie the bone fracture zone. Therefore the area moment of inertia and the polar moment of inertia for the bridges can be further reduced relative to the nodes, or changed for different portions of the plate, by modification of the relative thickness of the plate at the bridges and nodes at these locations. Moreover, maintaining the increased thickness of the plate at the nodes 520 surrounding reduced thickness bridges 522 prevents deformation of the screw holes in such nodes when plate bending. Optionally, the nodes can be selectively increased in thickness in areas surrounding anticipated plate bending.

Figure 28:
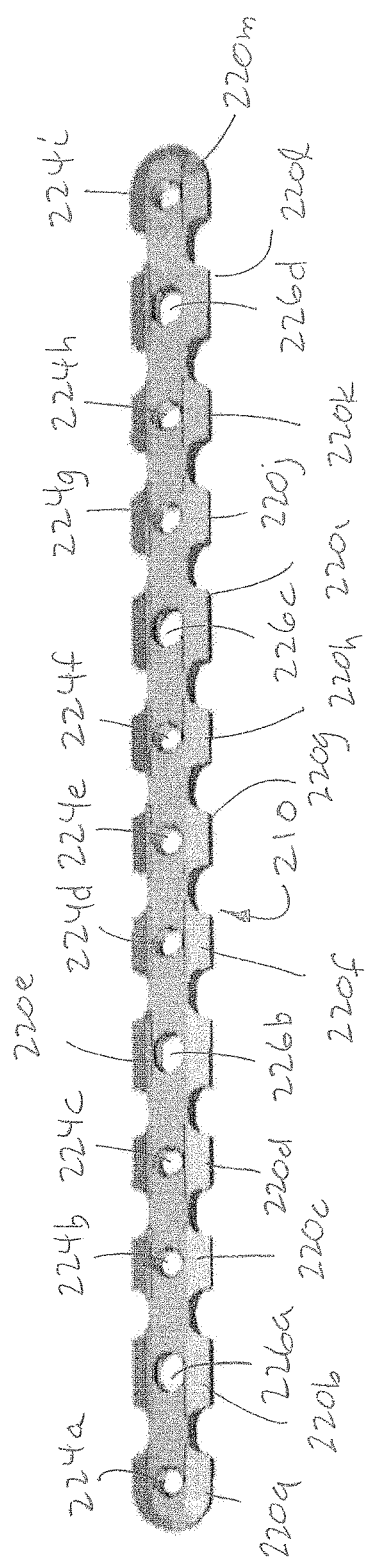
FIG. 28 is a perspective view of another plate according to the system described herein.

Turning now to FIG. 28, a second shape of bone plate 210 preferably provided with the system is already both planar and straight. As described above with respect to bone plate 10, each of the first and second sides of bone plate 210 are preferably adapted with the same structure and contours such that either surface of the plate may be positioned against the bone with equal effect. In addition, the plate 210 defines nodes, wing structures, rails, channels, and bridges of the same structure as in the cross-arm first plate 10. In one preferred design, each straight second plate 210 has a nodal arrangement with thirteen holes, including threaded circular holes and preferably non-threaded, elongate (in the direction of the longitudinal axis of the plate; i.e., non-circular, e.g., oval) holes that are preferably the same size, shape, and structure as holes 24, 26, describe above, so that common fasteners may be used with each. In this design, from one end of the bone plate 210, the plate has a first node 220a with a threaded circular hole 224a, then a second node 220b with an elongate hole 226a, then third and fourth nodes 220c, 220d with threaded circular holes 224b, 224c, then a fifth node 220e with elongate hole 226b, then sixth, seventh, and eighth nodes 220f, 220g, 220h with threaded circular holes 224d, 224e, 224f, then a ninth node 220i with an elongate hole 226c, then tenth and eleventh nodes 220j, 220k with threaded circular holes 224g, 224h, then a twelfth node 220l with an elongate hole 226d, and finally a thirteenth node 220m with a threaded circular hole 224i.

The plate 210 can be broken at a selected bridge to separate the plate 210 into two or more plate portions. By way of example, the plate can be subject to reverse bending at a central bridge between nodes 220f and 220g to provide a first plate portion having four nodes with threaded circular holes (220a, 220c, 220d, 220f) and two nodes with non-circular holes (220b, 220e), and a second plate portion having five nodes with threaded circular holes (220g, 220h, 220j, 220k, 220m) and two nodes with non-circular holes (220i, 220l).

Figure 11:
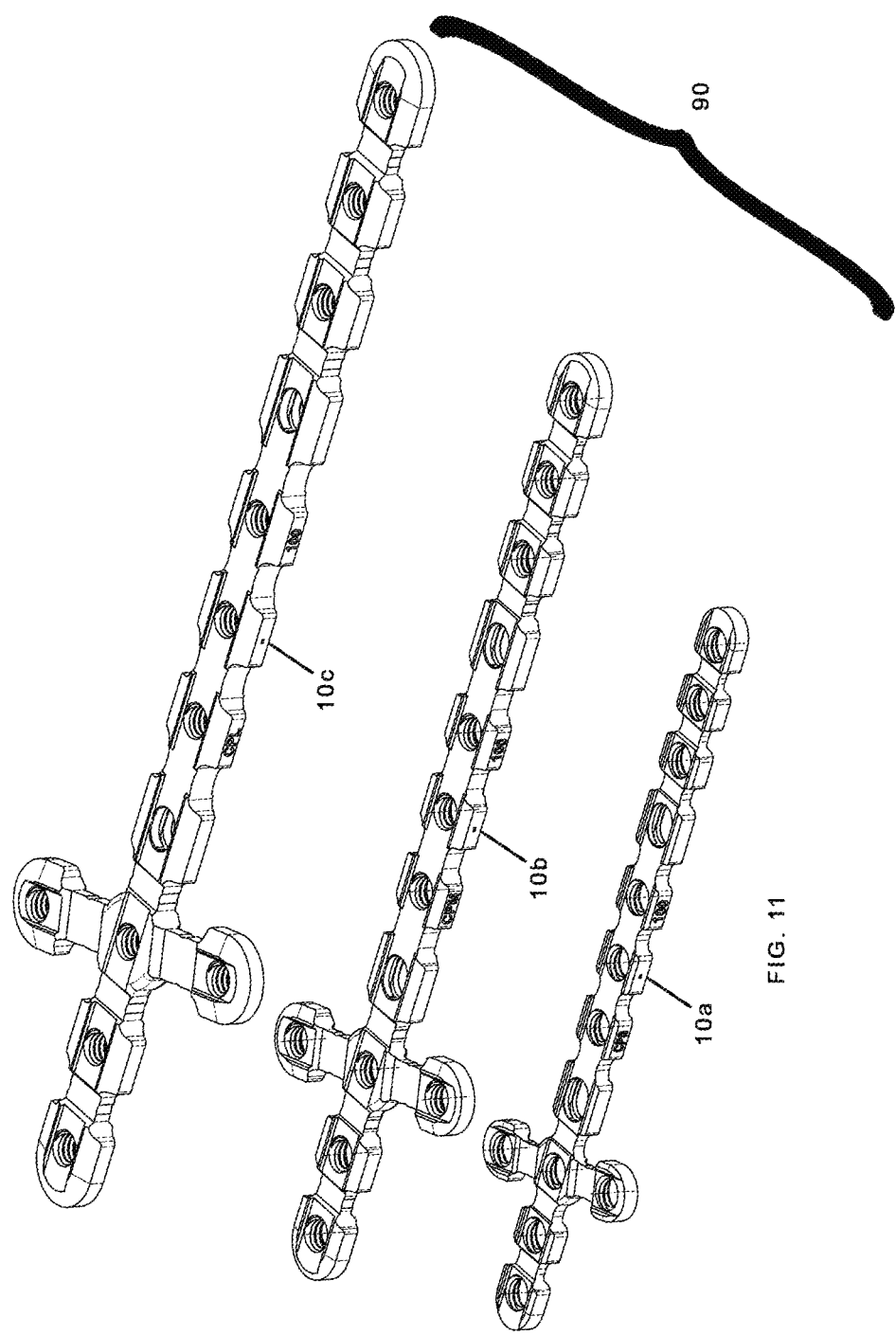
FIG. 11 is a perspective view of a set of plates of the type shown in FIG. 1.
Figure 29:
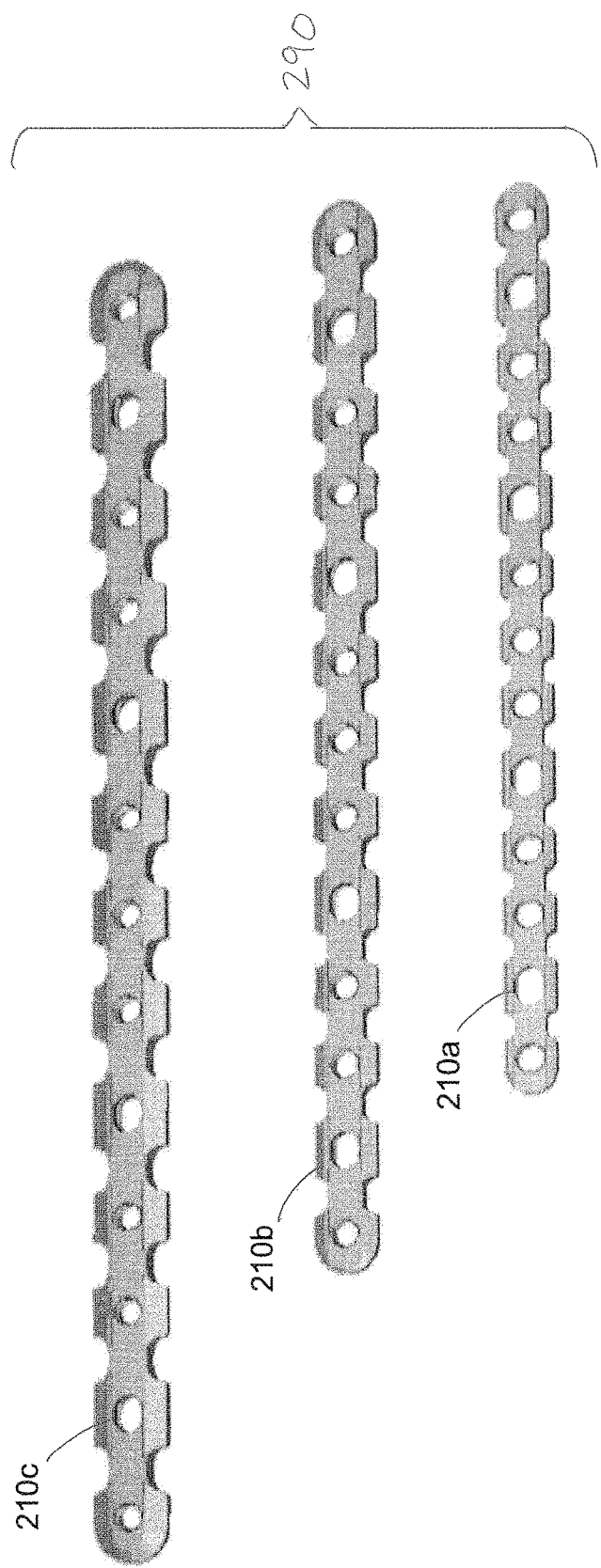
FIG. 29 is a perspective view of a set of plates of the type shown in FIG. 28.

Referring to FIG. 11, in accord with another aspect of the system, a limited set 90 of bone plates 10, each of like design but of a different size, are provided that can be adapted for treatment of many different types of bone fractures and bone sizes. The set preferably includes exactly three first plates, generally a relatively small size plate 10a, a relatively medium size plate 10b, and a relatively large size plate 10c, each for appropriate applications. Similarly, referring to FIG. 29, the system preferably includes a limited set 290 of straight bone plates 210, each of like design but of a different size, are provided that can be adapted for treatment of many different types of bone fractures and bone sizes. The set 290 preferably includes exactly three plates, generally a relatively small size plate 210a, a relatively medium size plate 210b, and a relatively large size plate 210c, each for appropriate applications. A fewer or greater number of plates can be provided in sets 90, 290, particularly depending on the population for which the plates are intended and their range of sizes. Such applications may be related to different size bones in the body of a patient, or bones in different patients of different sizes. While the plate can be used in a human population, the plates are particularly adapted for veterinary use, where the animals requiring treatment have a significant range in size between, e.g., small cats to large dogs. By way of example, the small plates 10a, 210a are sized to accommodate mammals of 5-15 kg, the medium plates 10b, 210b are sized to accommodate mammals of 15-25 kg, and the large plates 10c, 210c are sized to accommodate 25-40 kg, though usage of the plates on mammals of various sizes other than those indicated by example is certainly anticipated.

Figure 12:
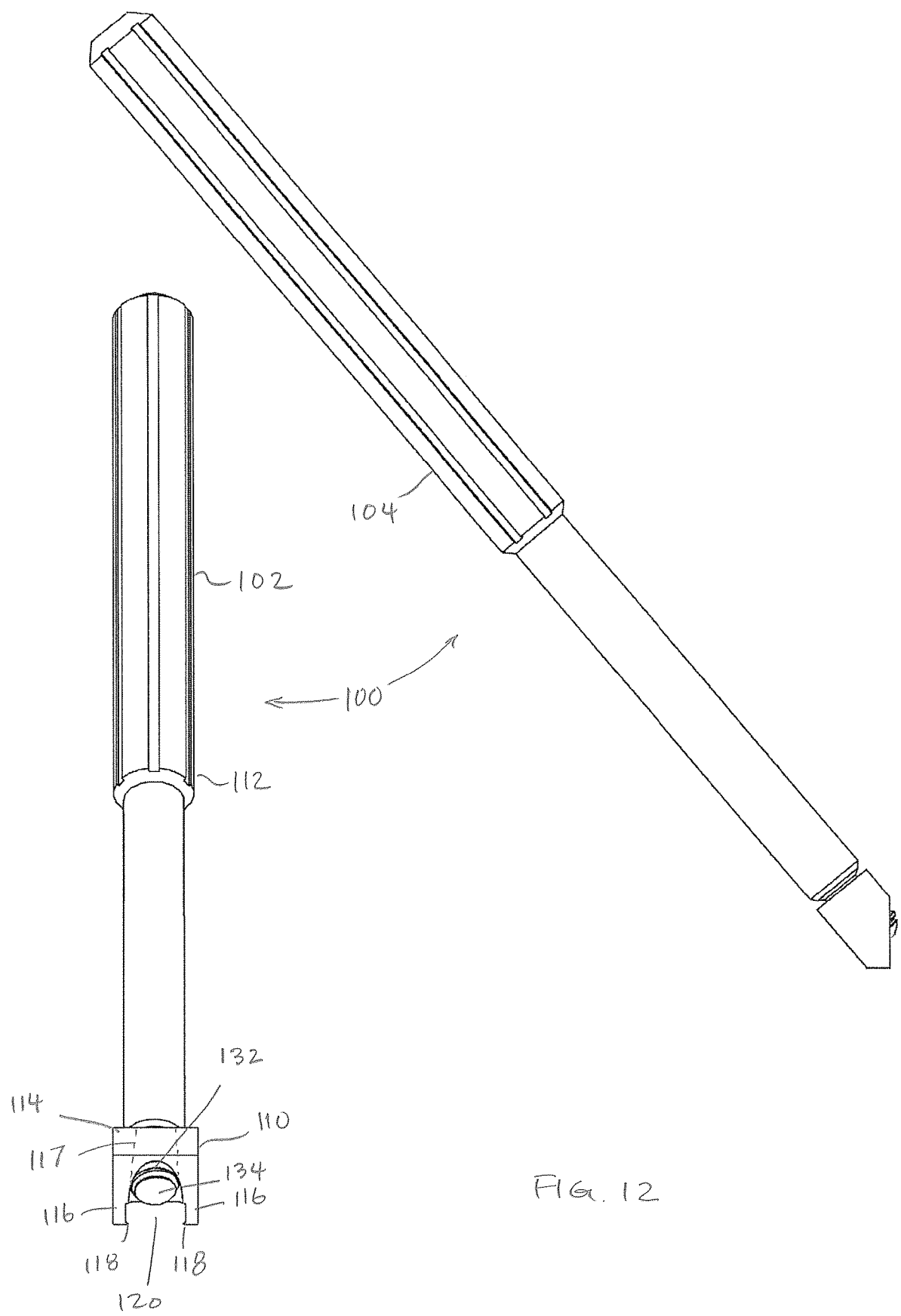
FIG. 12 shows a pair of plate benders, one in front view and one in side elevation view.
Figure 13:
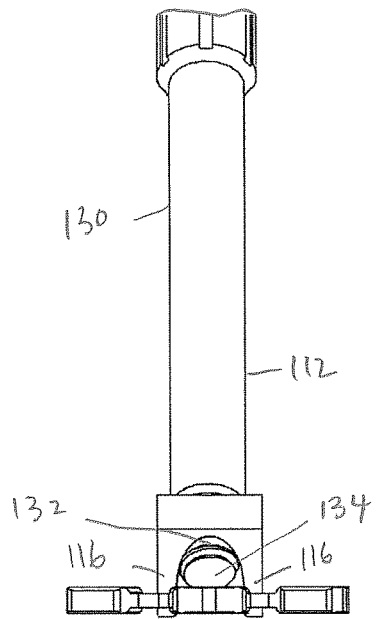
FIG. 13 shows, in a front view, a system of a plate bender coupled to a plate.
Figure 14:
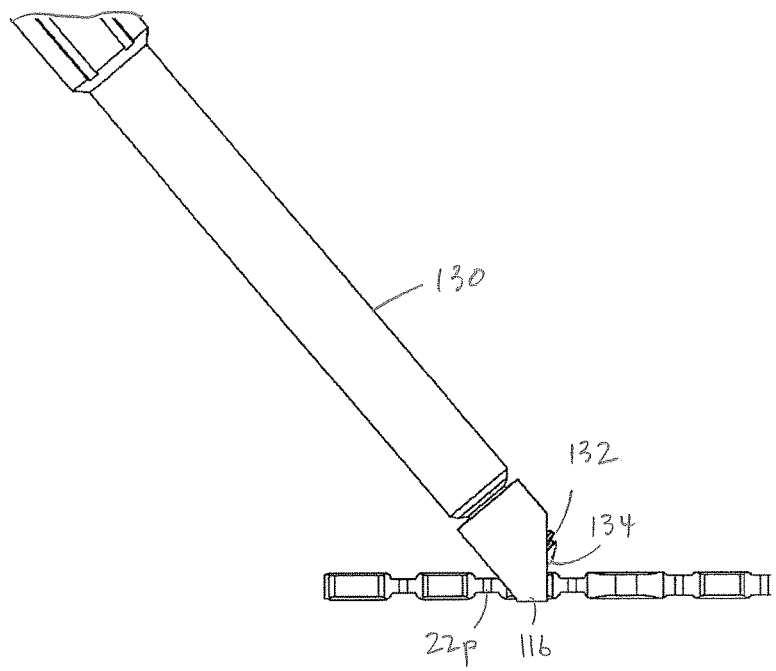
FIG. 14 shows, in a side elevation view, the system of FIG. 13.
Figure 15:
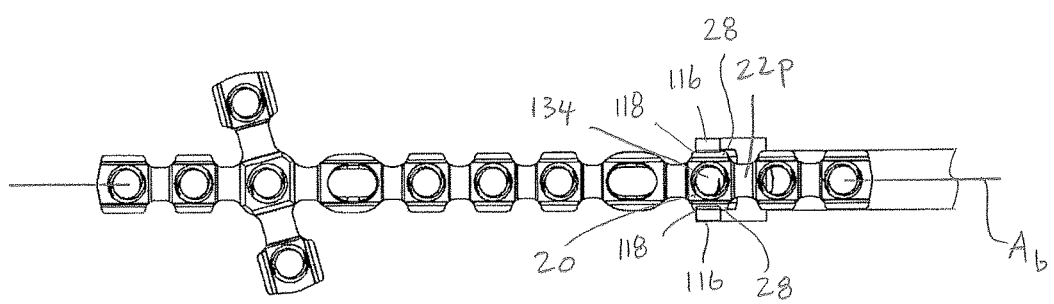
FIG. 15 shows, in a bottom view, the system of FIG. 13.

Turning now to FIG. 12, in accord with another aspect of the system, a bending system 100 is provided to bend the plate 10 out-of-plane at a preferably thinner bridge $20_p$ between two nodes 22. The bending system 100 includes first and second benders 102, 104, each of preferably like structure and assembly. With respect to bender 102, the benders each include a first type of clamp bracket 110 and a handle 112. The first type of clamp bracket 110 includes a body 114, an upper threaded hole 117 defined in the body 114, and a pair of spaced-apart arms 116 descending from the body, which each terminate in an inwardly directed seat 118. A space 120 is defined between the seats 118 at the lower ends of the arms 116. The threaded hole 117 has an axis that extends into the body 114 at a transverse angle relative to the extension of the arms 116 from the body 114 and a lower surface of the arms. Referring to FIGS. 13 through 15, the space 120 between the seats 118 is sufficient to be received vertically over a bridge 22p of the plate but too small to accommodate vertical passage over the wings 28 of an adjacent node. However, the space 120 between the arms and above the seats 118 is sized to allow the arms to be moved along an axis, e.g., $A_b$ from a bridge 22p to an adjacent node 20. The handle 112 includes a proximal shaft 130 rotatably fixed to a distal threaded clamping bolt 132, which is threadedly coupled within the upper threaded hole 117 of the bracket 110 and can be advanced toward (or away from) the seats 118 by rotation (or counter-rotation) of the handle 112 relative to the bracket 110. The end 134 of the clamping bolt 132 is convex and sized to seat against the countersink 32 of a threaded screw hole 24. In a closed clamping position, the handle 112 preferably extends at a transverse angle relative to an axis of the threaded screw hole 24, but may alternatively extend at a 90° angle.

In use, an appropriate sized plate 10 is selected for a bone, such as a long bone or the pelvis. The orientation of the plate 10 is selected such that one of the first and second sides 16, 18 is identified for placement against the bone. The plate is then reshaped, as necessary, and secured to the bone. The plate may be fully or partially reshaped before any attachment to the bone, or may be preliminarily attached to the bone, e.g., via a compression screw at a elongate slot 26, or one or more locking screws at screw holes 24, and then reshaped to accommodate the anatomical contours of the bone. The plate is then further secured with compression screws or fixed angle screws at the threaded holes 24.

More particularly, to reshape the plate 10 at, for example, a bridge 22p, the pair of benders 102, 104 are positioned on the plate at two nodes 20 on opposite sides of the bridge 22p of plate 10. (FIGS. 16A and 16B) (It is appreciated that bridges 22c can also be bent, though they are more rigid than bridges 22p.) The two nodes at which the pair of benders 102, 104 are coupled may be consecutive nodes directly in contact with bridge 22p, or may be spaced apart from bridge 22p by one or more other nodes. If necessary, for each bender, the handle 112 is counter-rotated relative to the clamping bracket 110 to partially withdraw the end 134 of the clamping bolt 132 from the space 120 in clamping bracket 110 until sufficient clearance is provided within the space for accommodating the thickness of the node 20. The benders are adapted for use on all of the sizes of the plates in the sets 90, 290. Each bender 102, 104 is placed over a bridge (FIGS. 17A and 17B) and then longitudinally slid into place onto its respective node 20 (FIGS. 18A and 18B). The seats 118 at the ends of the arms 116 are able to grab under the wings 28 (elevated off the bone due to their taper), even when the plate 10 is seated on bone. Then the handle is rotated relative to the bracket to advance the end 134 of the clamping bolt 132 against the upper surface (e.g., first side 116) of the plate at the countersink 32. It is appreciated that when the handle 112 is rotated, the clamping bracket 110 is stably maintained in position on the plate by the engagement of the arms 116 about the wings 28 of the node. The handle 112 is rotated until the plate is clamped between the end 134 of the clamping bolt 132 and the seats 118 on the arms. The bolt 132 is sized to seat on the countersink 32 and not enter the threaded screw hole 24 (FIG. 3). Thus, the end 134 of the bolt cannot deform the threads of the screw hole 24. When the bolt 132 is tightened against the plate 10, the end 134 of the bolt on one side of the plate and the seats 118 at the opposite side of the plate provide three points of contact against the plate for stably gripping the plate. Once each bender 102, 104 is stably coupled to its respective node, a relative force is applied between the benders to deform the bridge $22_p$ therebetween and thereby shape the plate 10 (FIGS. 20A and 20B).

Figure 30:
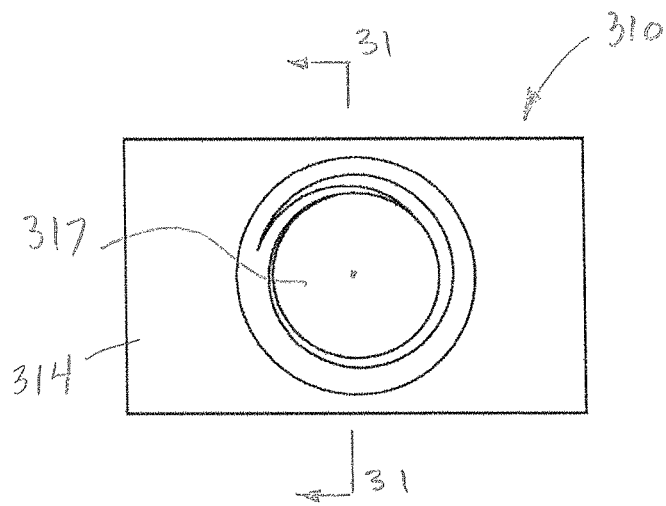
FIG. 30 is a top view of a clamping bracket of the system.
Figure 31:
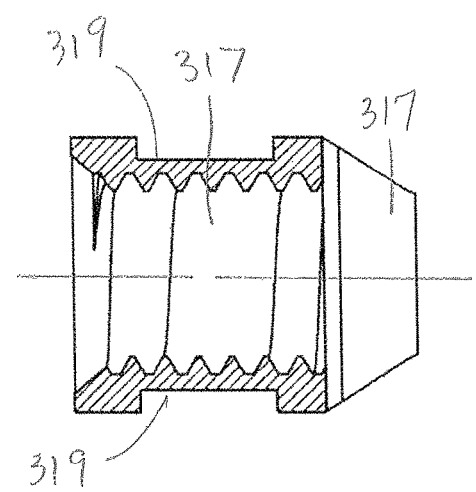
FIG. 31 is a section view across line 31-31 in FIG. 30.
Figure 32:
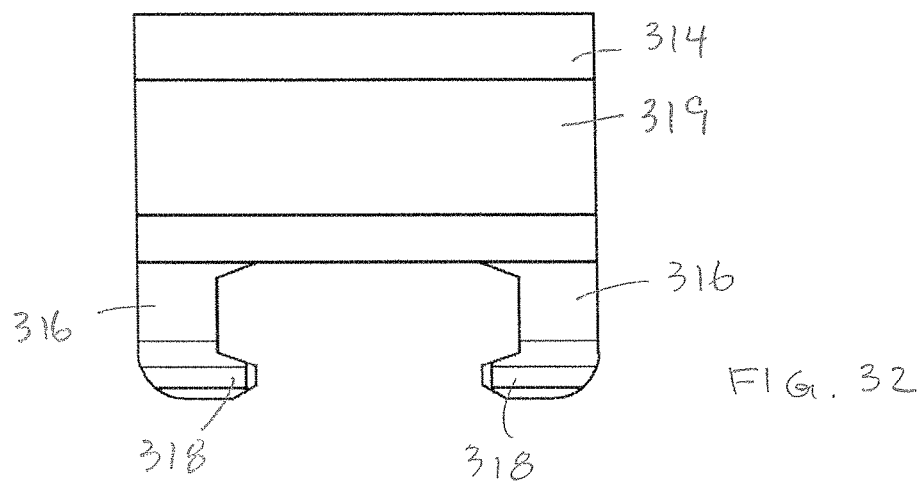
FIG. 32 is a side elevation view of the clamping bracket of FIG. 30.
Figure 33:
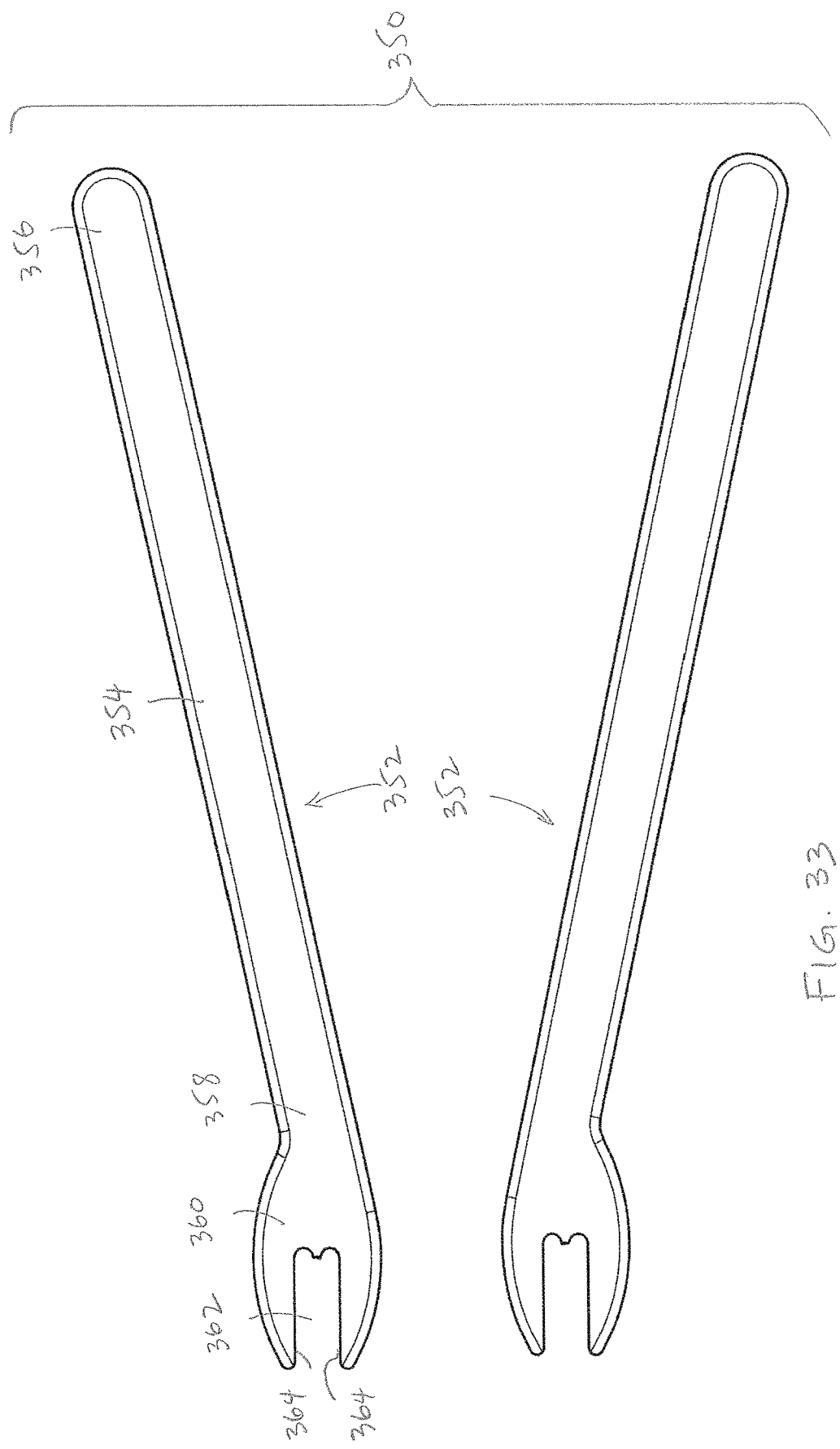
FIG. 33 is a plan view of a second pair of plate benders of the system.

Turning now to FIGS. 30 through 32, the bending system 100 may also be adapted to bend a plate "in plane". For such bending, the bending system 100 further includes second type clamp brackets 310. The clamping brackets 310 each include a body 314, a pair of spaced-apart arms 316 descending from the body, each arm 316 terminating in an inwardly directed seat 318, and an upper threaded hole 317 defined in the body 314, all similar to the first type of clamp bracket. However, in distinction, the threaded hole 317 has a central axis extending between and parallel to the extension of the arms 316 and the sides of the body 314. Further, parallel sides of the body transverse to the arms 316 are provided with recessed, parallel channels 319. Referring now to FIG. 33, in association with clamping brackets 310, the bending system also includes a pair 350 of reversible flat bending irons 352. Each bending iron 352 includes a handle 354 having a proximal end 356 and a distal end 358, and a flat head 360 extending at an oblique angle from the distal end 358. The head 360 includes an open mouth 362 with parallel sides 364 configured to stably engage within the parallel channels 319 of the clamping bracket 310.

Figure 34:
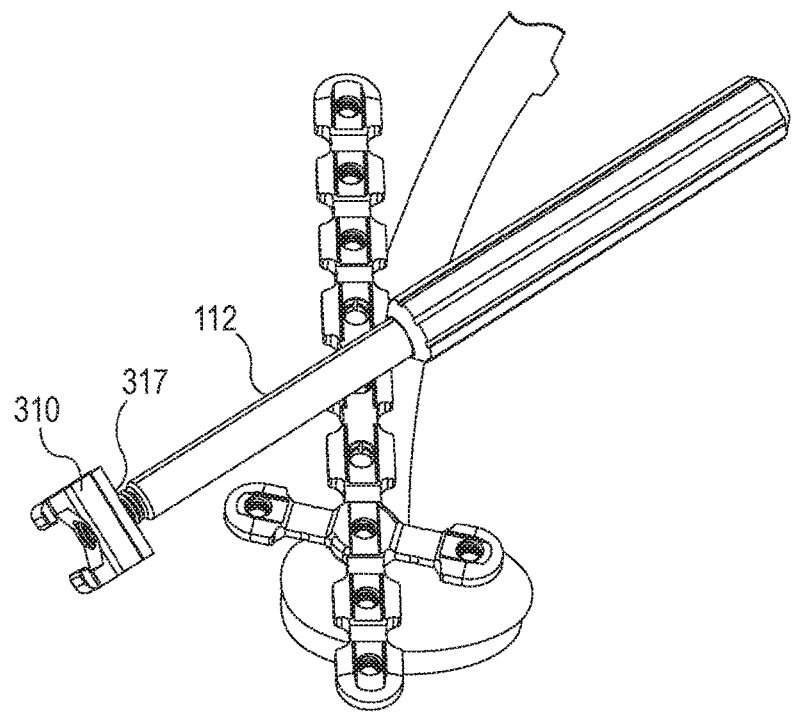
FIGS. 34 through 43 illustrate another method of bending plates of the system.
Figure 35:
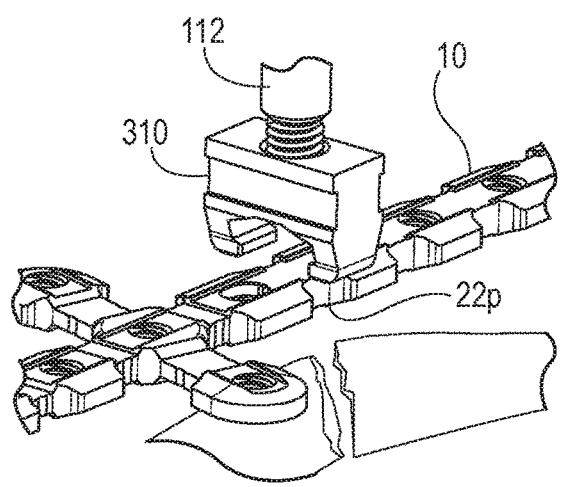
Figure 36:
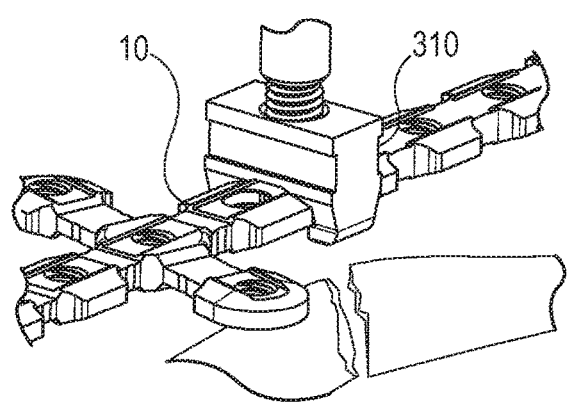
Figure 37:
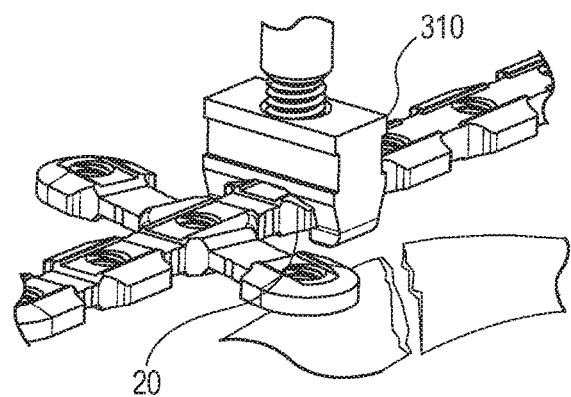
Figure 38:
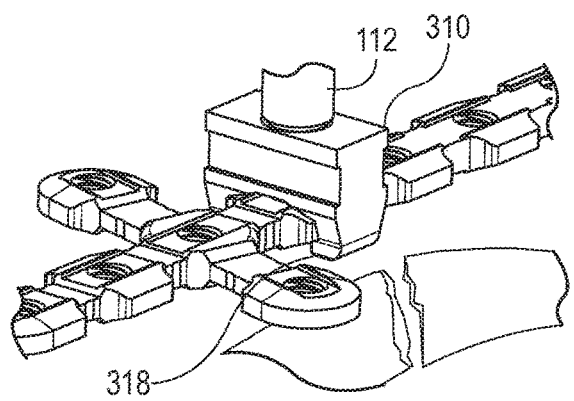
Figure 39:
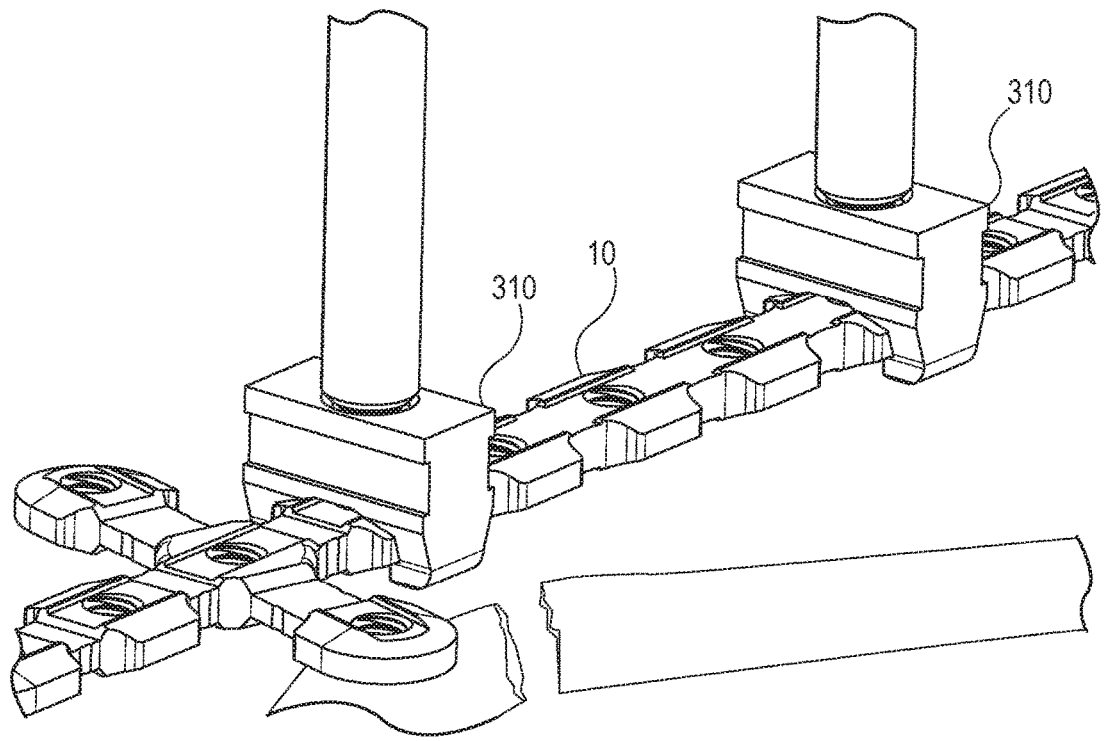
Figure 40:
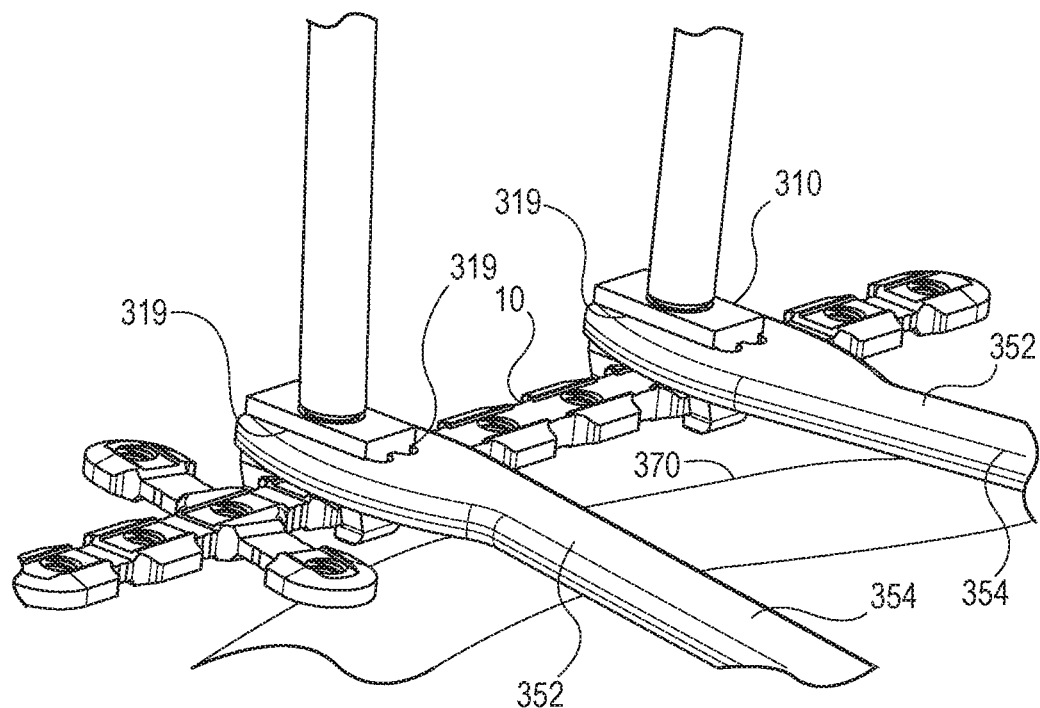
Figure 41:
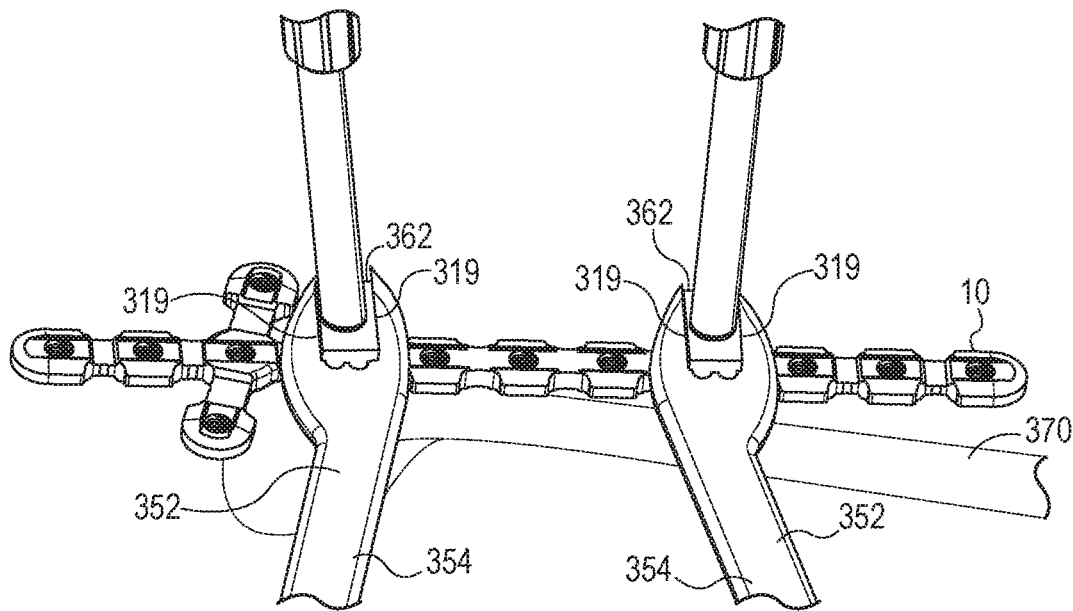
Figure 42:
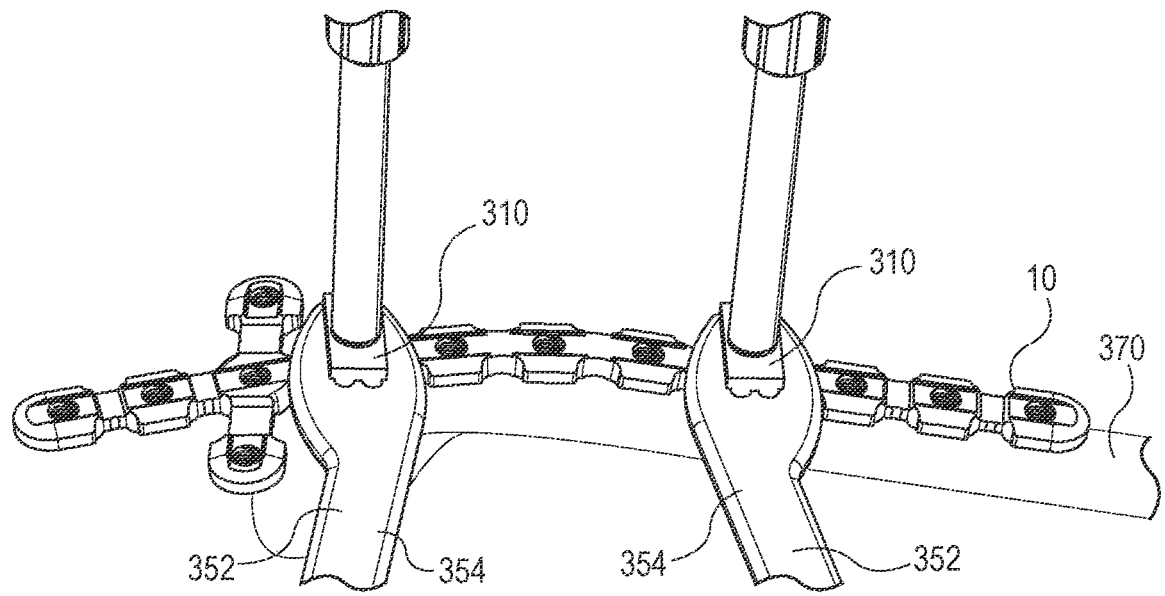
Figure 43:
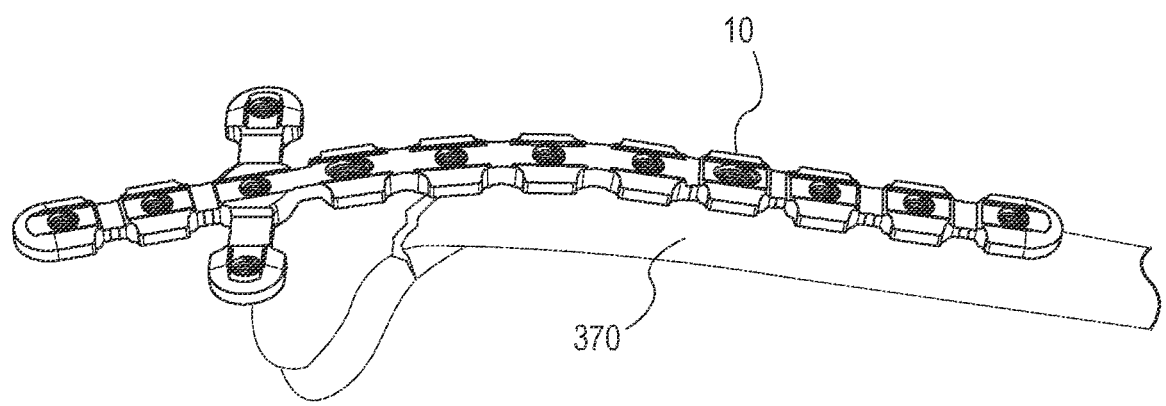

Turning to FIGS. 34 through 43, in use, handle 112 is partially inserted into the threaded hole 317 of the second-type clamp bracket 310 to engage the two components together (FIG. 34). The user then manipulates the handle 112 to advance the clamp bracket 310 onto the plate 10 at a bridge 22p (FIGS. 35-36), and then displaces the clamp bracket 310 onto a node 20 (FIG. 37). The handle 112 is then rotated relative to the clamp bracket 310 to further advance the end 134 of the clamping bolt 132 (FIG. 12) into the hole 317 of the plate 10 to clamp the node 20 between the end 134 and the seats 318 of the clamp bracket 310 (FIG. 38). A second clamping bracket 310 is similarly advanced onto the plate 10 (FIG. 39). All of the above is generally as described above with respect to bracket 110. The mouths of the bending irons 352 are then coupled to the clamp brackets 310 at the channels 319, preferably with the bending iron handles 354 angled away from each other (FIGS. 40-41). An angular force is then applied to the proximal ends 356 (FIG. 33) of the bending iron handles 354 to displace the clamp brackets 310 relative to each other and consequently deform the plate 10 into alignment with the bone 370 (FIG. 42). The bending irons 352 and clamping brackets 310 are then removed from the plate 10, and the contour of the plate 10 relative to the bone 370 is assessed to determine whether the plate suitably conforms to the anatomy (FIG. 43).

Turning now to FIGS. 57 through 59, another bending system 800 is provided to bend plate 210a (or any other plate described herein) at a preferably thinner bridge $220_p$ between two nodes 222. The bending system 800 includes first and second benders 802, 804. The first bender 802 includes a bending post element 806 and a separate clamping bolt 808. The post 806 includes a distal end integrally defining a first-type clamp bracket 810, and a proximal handle portion 812. The first-type clamp bracket 810 has substantially the same structure described above with respect to first-type clamp bracket 110. An axial throughbore 815 is provided through the post 806. The throughbore 815 includes a threaded distal end. The first-type clamp bracket 810 is configured to couple the post 806 over a hole of the plate 210a such that the longitudinal axis of the post 806 extends at an acute angle relative to the plane of the plate 210a. In an embodiment, the clamping bolt 808 includes a central shaft 820, an enlarged proximal knob 822, a threaded distal portion 824, and a convexly rounded distal tip 826. The shaft 820 of the clamping bolt 808 is extended within the throughbore 815 of the post 806, with the threaded distal portion 824 of the clamping bolt 808 in engagement with the threaded portion of the throughbore 815. Rotation of the knob 822 advances and retracts the rounded distal tip 826 from between arms 816 of the first-type clamp bracket 810. The second bender 804 is substantially the same as first bender 802. According to one distinction, the distal end of the bending post element 836 of the second bender 804 includes an integrally defined second-type clamp bracket 830. The second-type clamp bracket 830 has substantially the same structure as described above with respect to the second-type clamp bracket 310. As a result, the post 836 of the second bender 804 is adapted to couple coaxially over a hole of the plate 210a such that the longitudinal axis of the post 806 extends orthogonally relative to the plane of the plate 210*a*. Another distinction is that the post 836 includes a proximal connector 832 and a stop 834, for the engagement and retention, respectively, of a bending iron 850, described below.

In one manner of use, the bending system 800 can be comprised of one of each of the first and second benders 802, 804, as shown in FIGS. 57 and 59, to effect out of plane bending. The benders 802, 804 are placed over a bridge and then longitudinally slid into place onto respective node 20 surrounding an inter-positioned bridge. With respect to each bender, the knob 822 is rotated relative to the threaded throughbore 815 to advance the distal end 826 of the clamping bolt 808 against the upper surface of the plate 210*a* at the countersink of the screw hole in the respective node. It is appreciated that when the knobs 822 are rotated, each of the first and second type clamp brackets 810, 830 are stably maintained in position on the plate by the engagement of the arms 816 about the wings 228*a* of the respective nodes. The knobs 822 are rotated until the plate 210*a* is clamped between the distal tips 826 of the clamping bolts 808, 808*a* and the seats 817 adjacent the distal ends of the arms 816. The distal tip 826 is sized to engage the countersink of the screw hole and not enter the threaded screw hole 224*a*. This prevents deformation of the threads of the screw hole 224*a*. The benders 802, 804 may be coupled in parallel steps or sequentially. Once each bender 802, 804 is stably coupled to its respective node, a relative force is applied between the benders in the direction of arrow $A_1$ to bend the plate portion under bender 802 relative to the plate portion under bender 804 to thereby deform the bridge 220$_p$ between the benders and reshape the plate out of plane. The different angles at which the benders are attached provide a space for movement of the benders which would not otherwise exist if both benders were coaxial to the holes in the plate and adjacent one another. The benders 802, 804 are then removed from the plate, and may optionally be positioned on nodes at either side of another bridge to further reshape the plate. This method of bending works well for bending specifically at a single bridge 220*p*. However, if the plate 210*a* requires more significant bending at several adjacent bridges all at once, additional leverage may be required.

Figure 60:
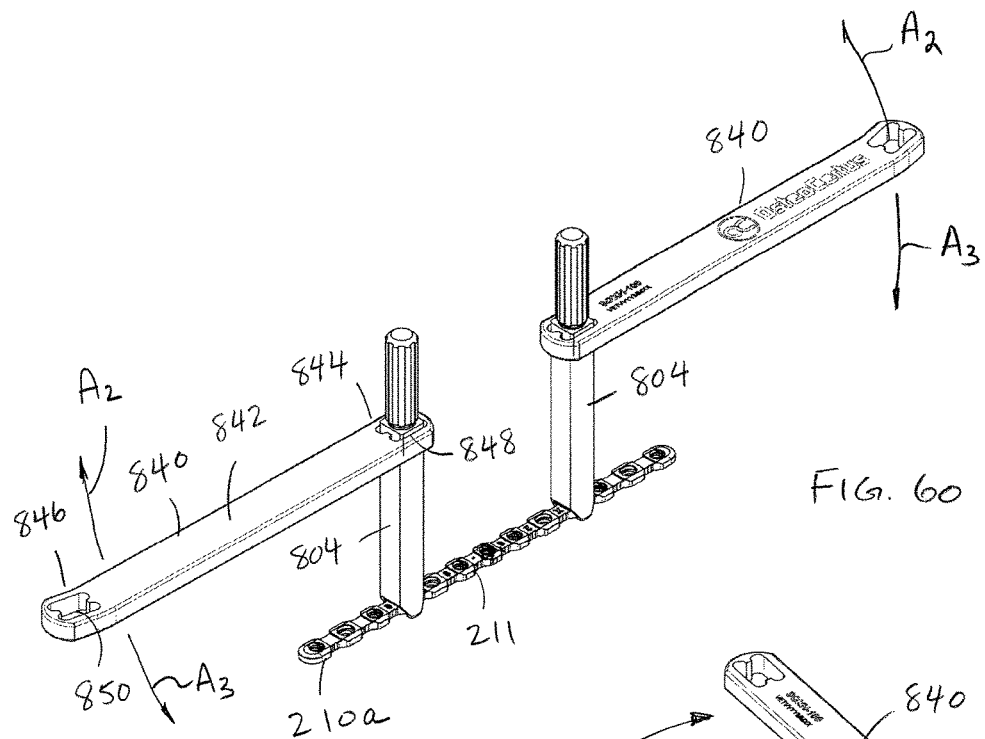
FIG. 60 is a top perspective view of the plate bender system in combination with a bone plate, with bending irons set up for out-of-plane bending of the bone plate.

Therefore, turning to FIG. 60 the plate bending system may also be comprised of two second benders 804 and two bending irons 840. The two second benders 804 are fixed to nodes of the plate, in the manner described above, at the longitudinal ends of the area 211 to be bent. The bending irons 840 include a shaft 842, a first end 844, and a second end 846 angularly offset (10-25°) from both the shaft 842 and first end 844. Each of the first and second ends 844, 846 includes an opening 848, 850 through the respective ends that is sized and shaped to fit over the proximal end of the post 836, and be rotationally fixed by connector 832 and stopped at stop 834 for stable bending iron engagement (FIG. 57). In one manner of reshaping the plate, the bending irons 840 are fixed in longitudinal alignment with the plate 210*a*. Then, a relative force is applied to the benders 804 by the bending irons 840 to move one or more of the benders upwards relative to the other (as shown by arrows $A_2$) or downwards relative to the other (as shown by arrows $A_3$) to effect a change in shape to the plate 210*a* that is out of the plane with the original planar extension of the plate.

Figure 61:
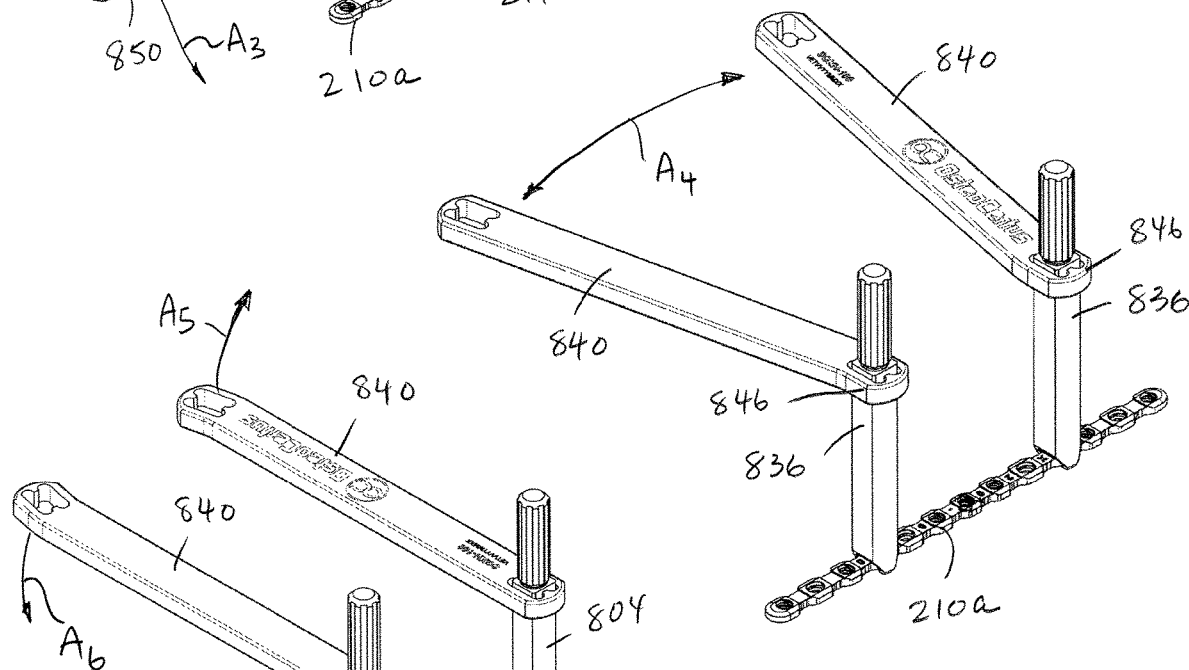
FIG. 61 is a top perspective view of the plate bender system in combination with a bone plate, with bending irons set up for in-plane bending about the longitudinal axis of the bone plate.
Figure 62:
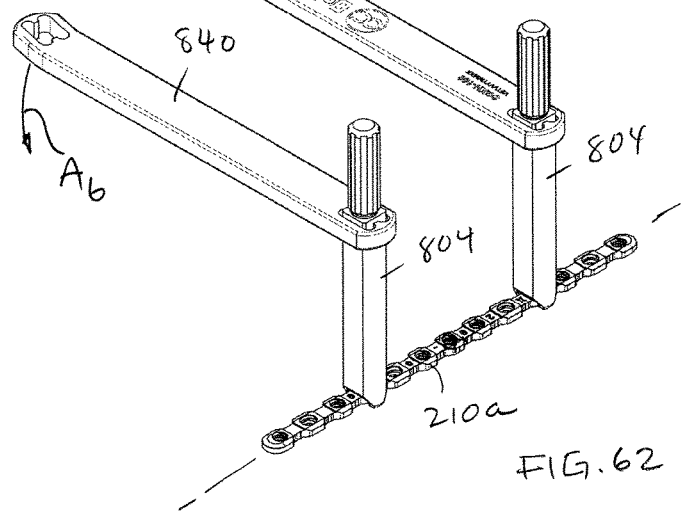
FIG. 62 is a top perspective view of the plate bender system in combination with a bone plate, with bending irons set up twist bending relative to the longitudinal axis of the bone plate.

Referring to FIG. 61, the bending irons 840 can be re-arranged on the posts 836 of second benders 804 such that the bending irons are attached to the posts 836 at their second ends 846. The bending irons 840 are further arranged such that they extend laterally relative to the longitudinal axis of the plate 210*a* and are angled apart from each other. Then, a relative force is applied to the benders 804 by the bending irons 840 to move one or more of the benders towards or away from the other (as shown by arrow $A_4$) to effect a change in shape to the plate 210*a* that is in the plane with the original planar extension of the plate. As shown in FIG. 62, the bending irons 840 can be further re-arranged on the posts 836 of second benders 804 such that the bending irons are attached to the posts 836 again at their first ends 844. The bending irons 840 are further arranged such that they extend laterally relative to the longitudinal axis of the plate 210*a* and are generally parallel to each other. Then, a relative force is applied to the benders 804 by the bending irons 840 to apply an upward force to one of the benders (as shown by arrow $A_5$), and a downward force to the other of benders (as shown by arrow $A_6$) to effect a change in shape to the plate 210*a* that exerts a twist along the longitudinal axis to effect reshaping of the bone plate.

Figure 63:
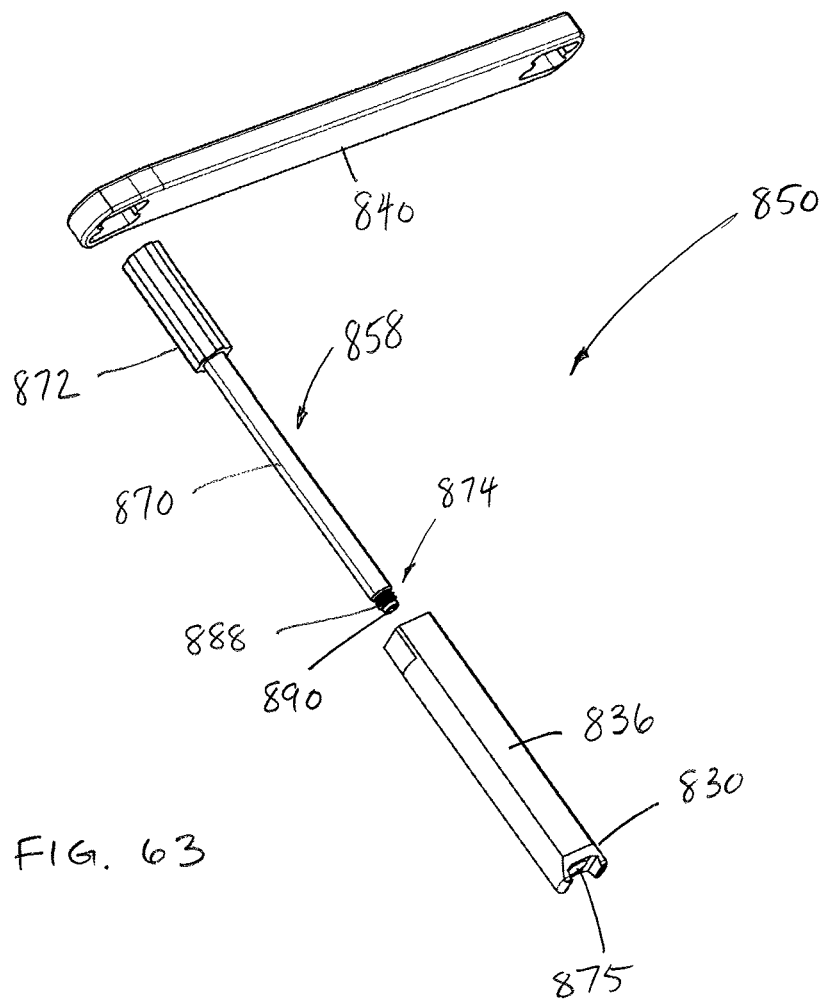
FIG. 63 is a perspective assembly view of another plate bender.
Figure 64:
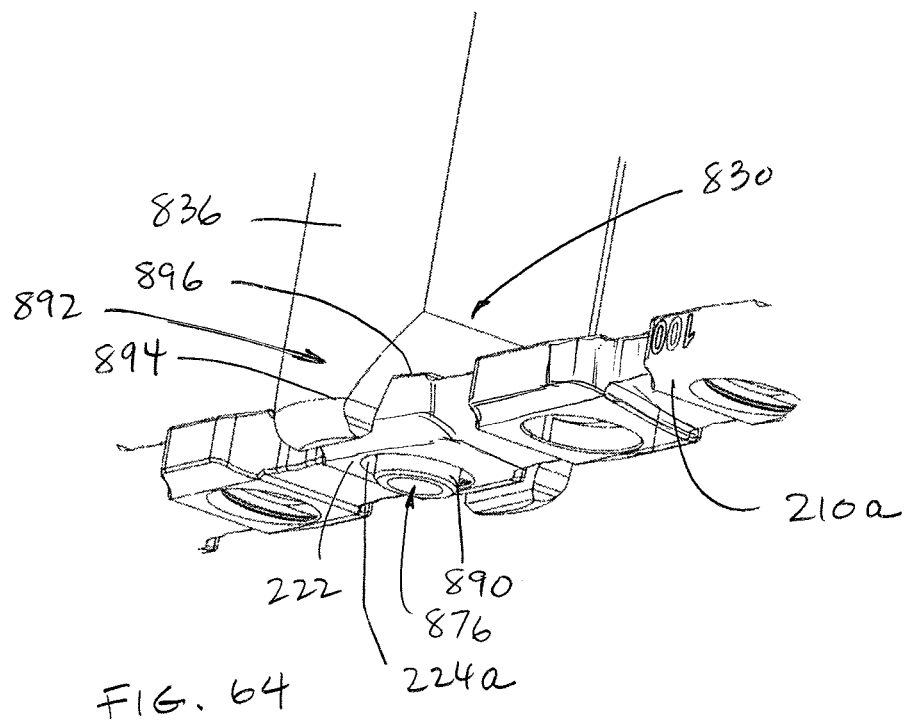
FIG. 64 is a bottom perspective view of the bender of FIG. 63 attached to the bone plate.

Turning now to FIGS. 63 and 64 another plate bender is shown. Plate bender 850 includes a post 836, a clamping bolt 858, and the same bending iron 840 as previously described. The post 836 has a non-threaded first throughbore 875 and a clamping bracket 892 at its distal end. The clamping bracket 892 includes side arms 894 that extends about the lateral sides of a plate and rotationally stabilize the bracket on a node 222 of the bone plate 210*a*. The clamping bolt 858 includes a shaft 870, a proximal knob 872, and a distal tip 874. A second throughbore 876 extends through the bolt 858. The tip 874 has a threaded portion 888 that is sized to threadedly engage a threaded screw hole 224*a* in a node 222 of the plate 210*a*. The tip 874 also preferably includes a non-threaded portion 890 that is sized to extend at least partially within the hole 224*a*. In assembly, the bracket portion 830 of the post 836 is positioned over the node 222, and the clamping bolt 858 is rotated to cause the threaded portion 888 to engage the screw hole 224*a*. The knob 872 of the bolt 858 is rotated until the node 222 of the plate is fixedly clamped relative to the threaded portion 888 and upper seats 896 adjacent proximal ends of the arm of the bracket 892. According to one aspect of the plate bender of FIGS. 63 and 64, the second throughbore 876 through clamping bolt 836 can be used as a drill guide for drilling holes in alignment with the axes of the screw holes in the plate. In addition, the drill guide can be used to guide K-wires for temporary fixation of the plate to the bone.

It is appreciated that the bending steps (out of plane bending, in plane bending, and twist bending) may be performed in any order and that bending steps may be repeated to effect bending in a stepwise manner. The bending may be performed in space, with the plate resting on a surface, or even with the plate positioned against the bone. The bending system 800 may include one first bender, two second benders, and two bending arms, such that all bending options; i.e., both out of plane and in plane bending, are permitted. Further, any subset of such components may be provided as a bending system.

While bending of the plate has been described using a pair of plate benders, the plate may also be bent using a single plate bender of the types described in conjunction with an alternate secondary plate stabilizer or bender. By way of example, the alternate secondary bender may comprise a shaft that threadedly couples to a node coaxial with a threaded screw hole. The shaft may threadedly engage the screw hole 24 to apply force to the node or maintain position of the node. Such an alternate bender may be preferred in circumstances where access to the bone does not readily permit use of the described benders.

Figure 21:
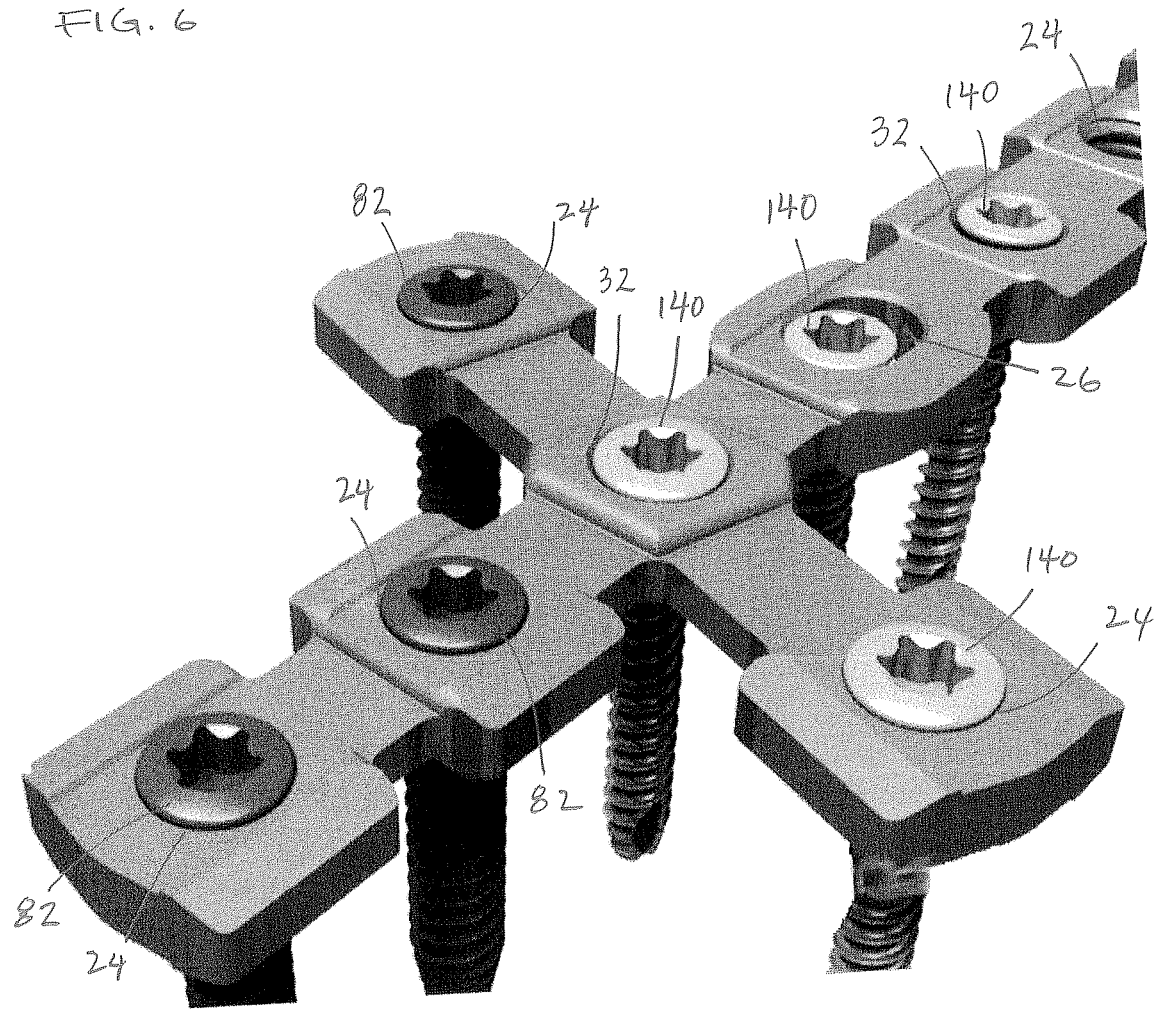
FIG. 21 is a broken perspective view of the system of a plate provided with screws.

As shown in FIGS. 6 and 21, the system also includes screws for securing the plate to the bone. In a preferred system, both locking screws 82 and compression screws 140 are provided. In addition, screws of different diameter and length are also provided for appropriate fixation and repair of the bone injury. The threaded screw holes 24 are adapted to receive both of the locking screws 82 and compression screws 140. The locking screws 82 threadedly engage with the threaded screw holes 24. The compression screws 142 having a lower head surface that engages the countersink 32 above the threads of screw holes 24.

Figure 22A:
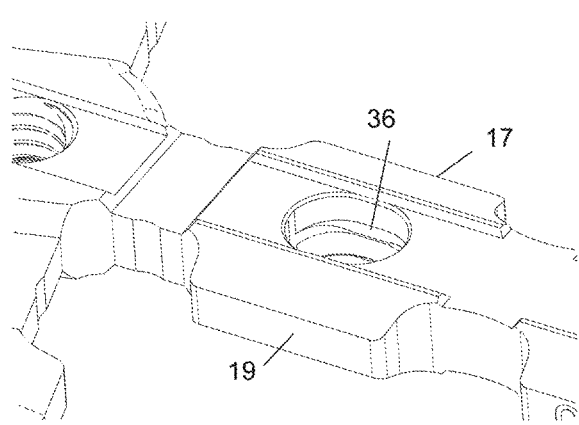
FIG. 22A is an enlarged perspective view of an elongate slot in the plate.
Figure 22B:
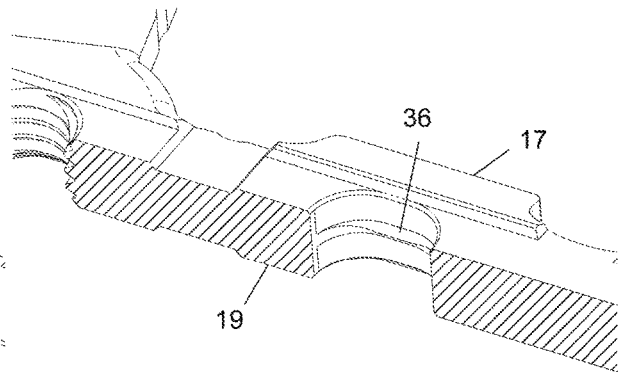
FIG. 22B is a view similar to FIG. 22A shown in longitudinal section.
Figure 23:
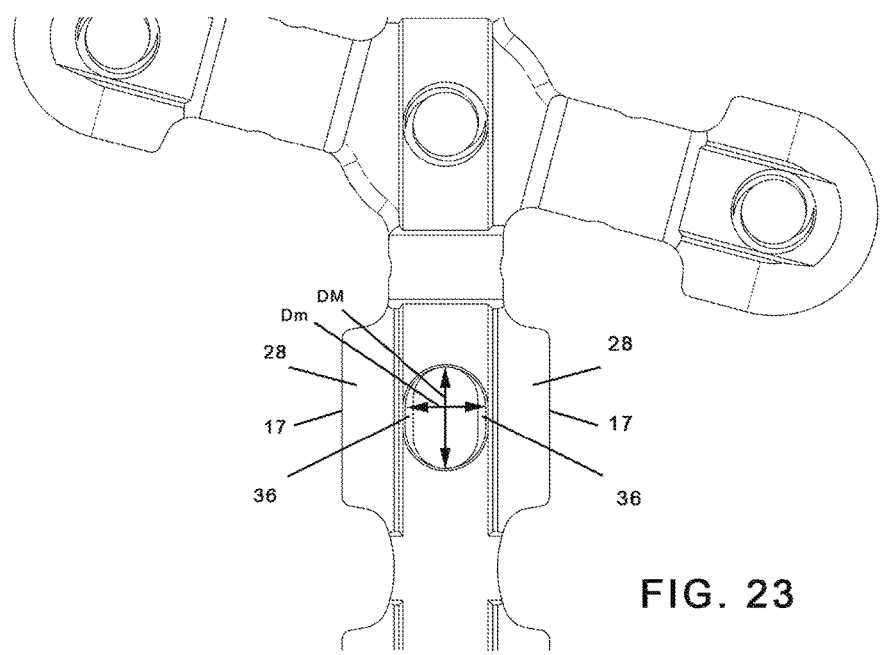
FIG. 23 is an enlarged partial plan view of a portion of the plate containing an elongate slot.

Turning now to FIGS. 22A, 22B and 23, the elongate screw holes or slots 26 have a major diameter $D_M$ and a minor diameter $D_m$. The slots include two thin ledges 36 extending along the long sides of the hole and parallel to the major diameter $D_M$. The ledges 36 have a thickness in the dimension extending between the first and second sides 16, 18, and parallel to the lateral sides 17, 19, of the plate. The ledges 36 taper toward the longitudinal axis of the plate at an angle. The ledges have a width in the lateral dimension. The ledges 36 are located recessed relative to each of the first and second sides 16, 18 of the plate, and more particularly located centrally between the first and second sides. As stated above, the wings 28 taper at a first angle.

Figure 25:
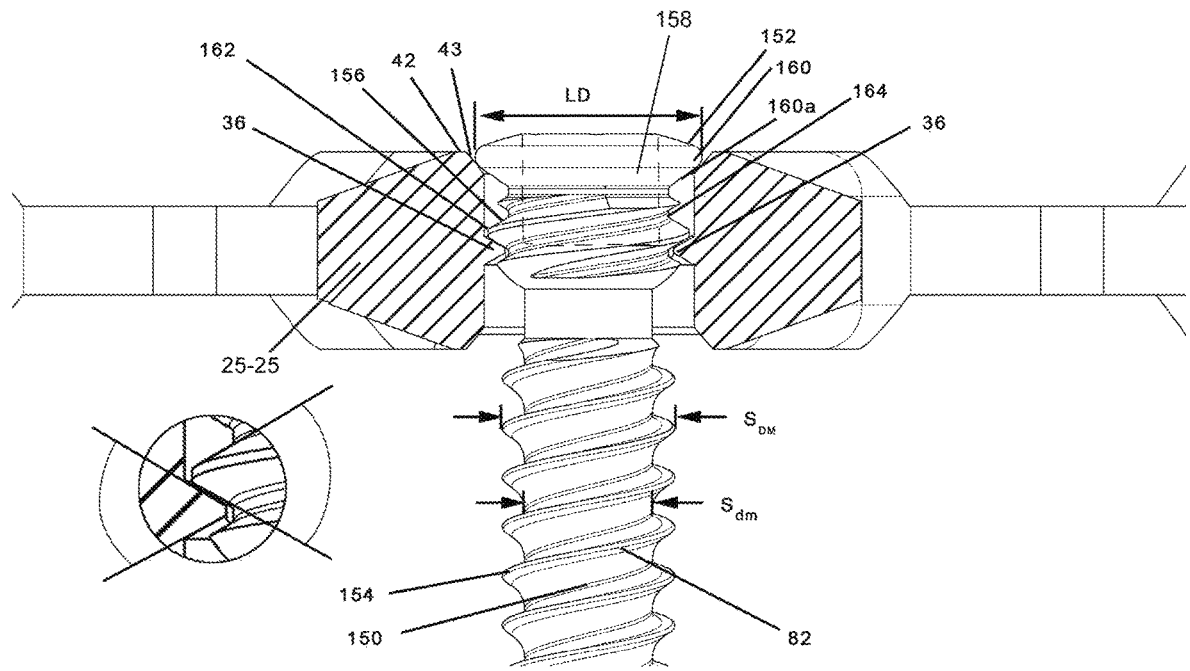
FIG. 25 is a cross-section across line 25-25 in FIG. 24.

Referring to FIGS. 24 and 25, the locking screws 82 each have a shaft 150 and a head 152. The shaft 150 includes bone-engaging threads 154 having a major diameter $S_{DM}$ and a minor diameter $S_{dm}$. The head 152 includes external threads 156, a driver slot 158 for receiving a driver, and an upper lip 160. The threads 156 define a first threaded pitch, a crest 162 (defining a major diameter $H_{DM}$), a root 164 (defining a minor diameter $H_{dm}$), and a thread angle between the crest 162 and the root 164. The thickness of the ledge 36 is less than the first thread pitch. The angle of taper of the ledge 36 is preferably substantially the same (±5°) as the thread angle between the crest 162 and root 164. The width of the ledge 36 is preferably approximate to, or slightly smaller than, the difference between the crest and root dimensions, or (major diameter−minor diameter)/2. The lip 160 has a diameter $L_D$ greater than the minor diameter $D_m$ of the elongate slot 26 (FIG. 23). The lower surface 160a of the lip 160 optionally extends at substantially a same angle (±5°) as the medial surfaces 43 of the rails 42. When the locking screw 82 is driven into the elongate slot 26, the ledge 36 functions as a single thread, and the threads on the head 156 threadedly engage the ledge. As such, the locking screw 82 is threadedly advanced into the plate relative to the ledge, and locked relative thereto. Also, the locking screw 82 can be advanced only until the lower surface of the lip 160 stops against the beveled medial surface 43 of the rail 42 laterally surrounding the slot, which forms a seat for the locking screw.

Figure 26:
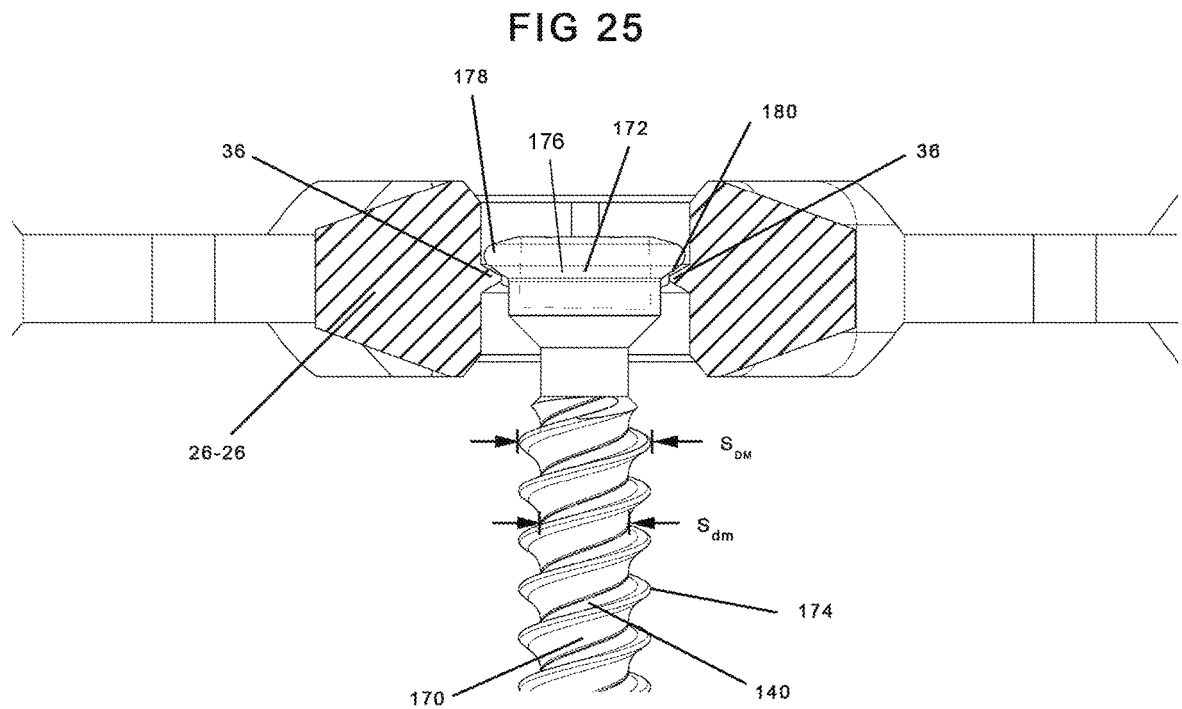
FIG. 26 is a cross-section across line 26-26 in FIG. 24.

Referring to FIGS. 24 and 26, the compression screws 140 each have a shaft 170 and a head 172. The shaft 170 includes bone-engaging threads 174 having a major diameter $S_{DM}$ and a minor diameter $S_{dm}$. The head 172 includes a driver slot 176 for receiving a rotational driver and an upper lip 178 that is smaller than a minor diameter of the slot 26 adjacent to, but not between, the ledges 36. The lower surface 180 of the lip 178 extends at an angle that preferably approximates the facing surface of the ledge 36. When the compression screw 140 is driven into the elongate slot 26, the ledge 36 functions as a stop which the lip 178 contacts in applying compression to the plate.

Figure 27:
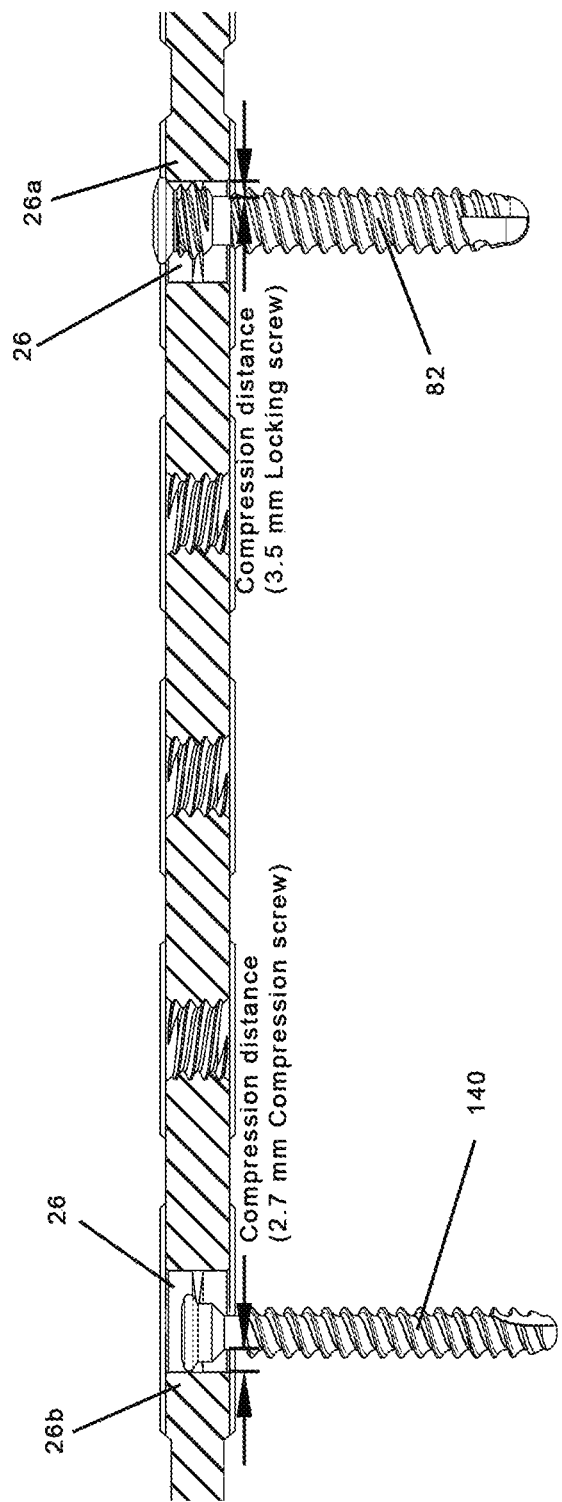
FIG. 27 is a longitudinal section view across the bone plate and screws shown in FIG. 24.

In addition, referring to FIGS. 24 and 27, each of the locking screw 82 and compression screw 140 are adapted to provide dynamic compression; i.e., longitudinal displacement across a fracture, as the respective screw is driven into a respective elongate slot 26. That is, when the screw is inserted at one end of the elongate slot, the head of the respective screw imparts a horizontal force component when driven vertically into contact against the plate. By way of example, locking screw 82 is inserted adjacent the end 26a of the slot in which displacement of the plate is intended. As the screw 82 is advanced toward a locking configuration with the plate, the head displaces the plate by up to a distance corresponding to (major diameter of the head thread−minor diameter of the shaft thread)/2. In one locking screw with a 3.5 mm shaft major diameter, the longitudinal displacement is (4.1 mm−2.6 mm)/2=0.75 mm. To effect dynamic compression with the compression screw 140, the screw is also inserted adjacent an end 26b of the slot in which displacement of the plate is intended. As the screw is advanced into compression against the plate, the head displaces the plate by up to a distance corresponding to (diameter of the lip at the head−minor diameter of the shaft thread)/2. In one compression screw with a 2.7 mm shaft major diameter, the longitudinal displacement is (4.1 mm−2.1 mm)/2=1.0 mm. As such, in the described set of locking screw and compression screw, the locking screw effects 75% of the longitudinal compression of the compression screw; this result is at the median of a preferred relationship (75%±15%, or 60%-90%) of the relative longitudinal, or dynamic, compression between the two types of screws.

Figure 48:
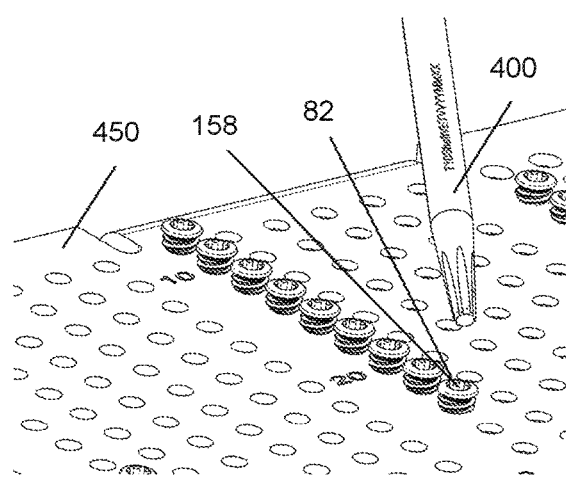
FIGS. 48 through 50 illustrate a method of using the screwdriver to pick up screws from a tray containing screws.
Figure 49:
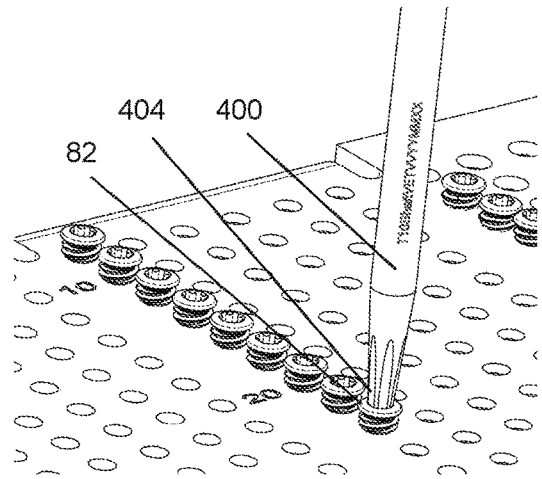
Figure 50:
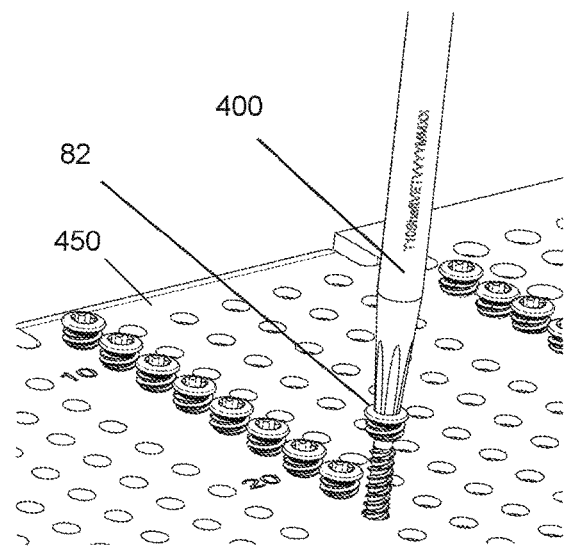

Turning now to FIGS. 44 through 46, a screwdriver 400 for picking up the screws 82, 140 and driving the screws through the screw holes 24, 26 and into the bone is provided. The screwdriver 400 includes a shaft 402 having a distal T10 torx (hexalobe) head 404 and a proximal end 406. The head 404 includes inner lobes 410 and outer lobes 412. The inner lobes 410 define a short (0.8 mm) distal portion 410a of straight milled grooves which continue into a proximal portion 410b of curved milled grooved (R=~38 mm). The short distal portion 410a aligns with the corresponding socket 158 in the screw 82, thus providing directionability. In distinction from a conventional hexalobe driver, the outer lobes 412 are not curved. Rather, the head 404 is turned on a lathe to define a 4.5 degree cone 418 that intersects the milled grooves 416 of the inner lobes 410. The cone 418 provides a combination of proper friction and good control of the tip length. Conventional friction angles of 3 degrees were found to provide too much variability to the length of the head that extends into the screw socket 158. This leads to the head 404 bottoming out within the screw socket with insufficient frictional engagement between the lobes 410, 412 of the head 404 and the socket 158 of the screw. Alternatively, with the head sitting too high in the socket, too little engagement is made between the inner and outer lobes 410, 412 and the socket 158 and there exists an associated potential for stripping the screw as a torque is applied. Also, both of these improper fits can result in tilt of the driver head 404 relative to the socket, and a lack of directionality. The actual frictional engagement between the head 404 and the screw socket results from the edges between the cone 418 and the grooves 410a, 410b, with such edges digging into a transition zone between the inner and outer corners of the socket 158 of the screw 82. This creates a high friction interface for engaging the screw. Referring to FIGS. 48 and 49, the head 404 is designed to self-orient axially into the screw socket 158 of screw 82 to a correct depth so that it does not alter the alignment (and thus the "directionability") of the screw 82 and has stability in the screw socket 158. In addition, the driver head 404 is configured and engages the screw socket 158 at a correct depth for generating a frictional engagement which allows the head 404 to pick up and withdraw the screw 82 from an array of screws in a tray 450, and also is adapted to apply significant torque to the screw 82 to insert the screw into bone (FIGS. 49-50). The use of driver head 404 to pick up and drive screw 82 is equally applicable to screw 140.

Turning back to FIGS. 44 and 45, an industry standard AO connector is provided to the proximal end 406 of the shaft 402 includes. The AO connector 406 includes a longitudinal flat 420 at one side and a peripheral groove 422 at its opposite side. In distinction from a standard AO connector, the proximal end 406 includes a threaded set screw hole 424 extending into the flat 420. With such structure, the shaft 402 can be positioned as a driver bit in powered driver with a mating AO socket structure. In addition, a handle 426 including a lateral hole 428 aligned with the set screw hole 424 can be assembled onto the same shaft, and secured to the shaft with a set screw 430 that engages the set screw hole 424. This permits the driver to be hand-operated. Thus no pressing, over molding or cross-pinning is required for the connection to a permanent (or semi-permanent) handle.

Turning now to FIGS. 51 through 55, the shaft 602 of another screwdriver 600 for picking up the screws 82, 140 and driving the screws through the screw holes 24, 26 and into the bone is provided. The screws 82, 140 are adapted with a square driver slot. The screwdriver 600 includes a shaft 602 having a distal head 604 and a proximal end 606. The head 604 is a driver defining side faces 610 in the form of a regular polygon. Most preferably, the head 604 defines a square driver tip. The side faces 610 of the head extend distally parallel to each other; i.e., they do not converge. The side faces 610 meet at corners 612 that are rounded by a taper that tapers toward the distal end. The taper is preferably a conical taper. The conically tapered corners 612 each provides a first radius to a corner at a relatively proximal location on the head that is larger than a second radius to the corner at a relatively distal location on the head. The conical taper is preferably between 3° and 5°. The head 604 may be formed obtaining a rod, squaring the sides of the end of the rod, and then rotating the squared sides on a lathe to define a tapered cone of the defined taper angle that intersects the corners of the square. The conically tapered corners 612 of the head 604 facilitate insertion of the tip into the screw head, and the faces 610 proper friction, directionality, and good control of the tip length. The shaft 602 may be permanently attached to a handle 626, or may be removably attached from the handle with, e.g., a set screw 628 or AO coupling, such as driver shaft 402 may be with respect to its handle 426.

Figure 56:
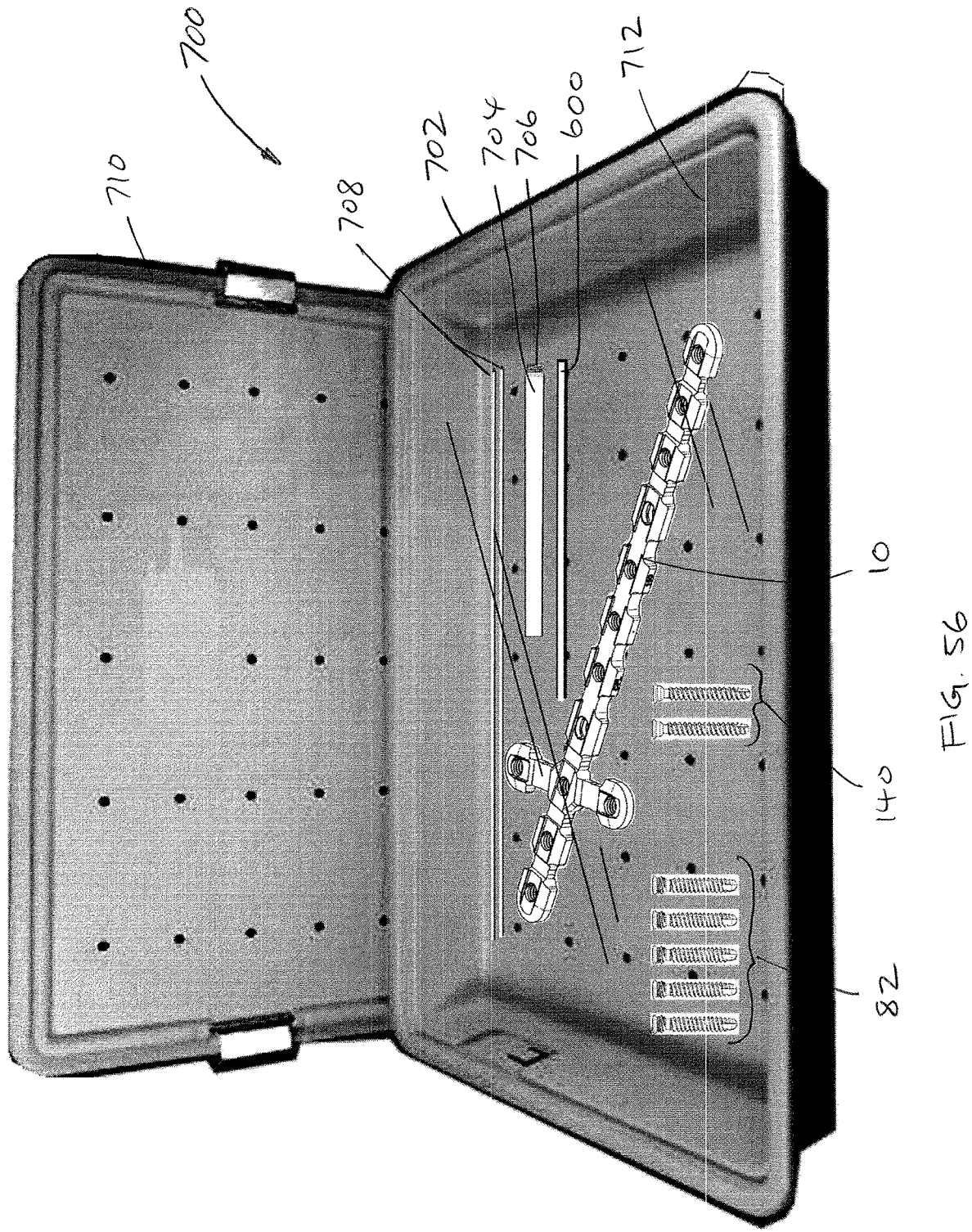
FIG. 56 illustrates an embodiment of a surgical kit described herein.

Turning now to FIG. 56, a single-use surgical plate kit 700 provided in a disposable container 702 is shown. The single use plate kit 700 preferably includes a single bone plate 10 (or 210) and a defined set of screws. The single use kits 700 are provided in separate configurations, with each configuration containing one of the different bone plates described herein (cross-arm or straight, and in each of various sizes). The set of screws preferably includes more locking screws 82 than non-locking screws 140. The kit most preferably includes five locking screws 82 of a first length, and two non-locking screws 140 of a second length, which is preferably the same or longer than the first length. This screw count and configuration provides sufficient hardware for fixation of most fractures with the bone plate 10 (or 210), without leftover screws as waste. The kit 700 permits a surgeon to acquire only the parts required for a procedure without de-sterilizing other parts and to maintain an efficient inventory.

The kit 700 may also include a tubular bending bar 704 having a threaded end 706 that can thread into any of the threaded screw holes in the nodes of the bone plate and apply a bending force to deform the plate at an adjacent bridge. This bending bar 704 can be used for less extreme plate bending than permitted by the other bending tools described herein. The kit may also include one or more K-wires 708. The K-wires 708 can function as a drill for pilot holes into the bone or for temporary or permanent fixation in association with the plate. The bending bar 704 may also function as a drill guide for the K-wires 708 to guide the K-wire coaxially relative to the screw hole in the plate to which the bending bar is inserted. The kit may also include a shaft 602 of a screwdriver 600 (or a complete screwdriver) for the screws. Alternatively, other drivers and/or plate benders can be provided in the kit. The kit 700 preferably consists of limited components so that whatever is not used can be disposed of with limited waste. As such, the kit may consist of any combination of plate and screws alone or in any combination with a bending bar, one or more K-wires, and at least the driver shaft portion of the screwdriver. The kit may be provided with all contents pre-sterilized and ready for use, or may facilitate the pre-surgical sterilization of the limited parts most commonly required for a surgical procedure.

The container 702 is preferably a surgical tray and is intended to be disposable. The container may be made, e.g., of metal, a polymer, cellulose fibers and/or combinations thereof. The container 702 may be provided with a lid 710 and/or a preferably transparent, thin wrapping 712 that covers the contents thereof. The container may alternatively or additionally comprise a box or other packaging that facilitates its storage and contents identity when used in a surgical facility.

The single-use plate kit 700 is intended to be used in conjunction with a re-usable set of more robust and costly instruments, several of which have been described herein. For example, the benders 102, 104, first-type clamping bracket 110, second-type clamping bracket 310 and bending iron 352, as well as drill bits, handles, etc. may all be provided as part of a re-usable instrument set that can be used in conjunction with the single-use plate kit 700. In addition, non-standard components, including screws shorter or longer than those provided with kit, can be provided separately on an as-needed basis.

The system provides two plate designs, each of which accommodates left and right anatomies and which can also be customized in shape via removal of one or more nodes and bending along one or more bridges. The plate designs are readily adaptable for treatment, even for those surgeons who have not had significant prior experience with anatomical or shapeable plates adapted for specific bones.

There have been described and illustrated herein several embodiments of a bone plate system including bone plates, plate benders, and screws, and methods of implanting the plate in bones of a mammal. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A set of bending tools for bending a bone plate, the bone plate having a first side, an opposite second side, and lateral sides extending between the first and second sides, the bone plate including a plurality of holes extending between the first and second sides, at least one of the set of bending tools comprising:
   a) a bracket having arms including seats at the end thereof, a space defined between the arms, the arms adapted to surround the lateral sides of the plate and the seats adapted to extend under the first side of the plate; and
   b) a handle movable relative to the bracket into and out of the space to contact the second side of the plate and clamp the plate between a portion of the handle and the seats of the bracket.

2. The set of bending tools of claim 1, wherein:
   the bracket of at least one of the bending tools includes a threaded hole, and the handle includes a threaded bolt threadedly engaged within the threaded hole, and the portion of the handle is movable relative to the space by rotation of the handle relative to the bracket.

3. The set of bending tools of claim 1, wherein:
   each of the bending tools has a bracket and a handle of a same construct.

4. The set of bending tools of claim 1, wherein:
   the bone plate extends within a plane, and the set of bending tools are adapted to apply a force to the bone plate to bend the bone plate within the plane.

5. The set of bending tools of claim 1, wherein:
   the bone plate extends within a plane, and the set of bending tools are adapted to apply a force to the bone plate to bend the bone plate out of the plane.

6. A plate bending system for bending a bone plate having a first side, an opposite second side, and lateral sides extending between the first and second sides, the bone plate including a plurality of holes extending between the first and second sides, the plate bending system comprising:
   a first bender and a second bender, each having,
   a) an element including an upper body with a bore, and arms descending from the body the arms having proximal and distal ends, a space defined between the arms and communicating with the bore, the arms adapted to surround the lateral sides of the plate, and a seat adjacent one of the proximal and distal ends of each arm, the seats adapted to contact at least one of the first and second sides of the plate;
   b) a bolt extending through the bore of the element, the bolt including a distal threaded end and a proximal manual engagement end, the distal end of the bolt adapted to contact one of the holes of the bone plate, wherein rotation of the bolt within the bore and relative to the plate causes the bolt to move into and out of the space and consequently clamp the plate between the bolt and the seats; and
   c) a handle couplable relative to the element, such that when the first and second benders are coupled to the bone plate, and a force is applied to the handle of each of the first and second benders, the force is transferred to the bone plate.

7. The plate bending system according to claim 6, wherein:
   the seats are adjacent the distal ends of the arms.

8. The plate bending system according to claim 6, wherein:
   the seats are adjacent the proximal ends of the arms.

9. The plate bending system according to claim 6, wherein:
   the bolt includes a throughbore.

10. The plate bending system according to claim 6, wherein:
    the plate bending system is adapted for use with a bone plate having a plurality of threaded holes each with a countersink, and the distal threaded end of the bolt is sized and shaped to stably engage within the countersink of the threaded holes of the bone plate.

11. The plate bending system according to claim 6, wherein:
    the handles are bending irons, each including a shaft, a first end, and a second end angularly offset from both the shaft and first end, and each of the first and second ends includes an opening that is sized and shaped to fit over a proximal end of the element and be rotationally fixed relative the element.

12. The plate bending system according to claim 6, wherein:
    the handle is flat and includes a first side and a second side, and the handle is reversible such that the distal end of the handle can be coupled to the element when either of the first or second sides of the handle faces the second side of the plate.

13. The plate bending system according to claim 6, wherein:
    the upper body of the element includes channels, and the distal end of the handle has an engagement portion that slides within the channels to rotationally fix the handle relative to the element.

14. The plate bending system according to claim 13, wherein:
    the channels are parallel, and the engagement portion includes two parallel sides surfaces that engage within the channels.

15. A bending tool for bending a bone plate, the bone plate having a first side, an opposite second side, and lateral sides extending between the first and second sides, the bone plate including a plurality of holes extending between the first and second sides, the bending tool comprising:
    a) a bracket having an upper body with a threaded hole, and arms descending from the body, the arms including seats at the end thereof, a space defined between the arms and communicating with the threaded hole, the arms adapted to surround the lateral sides of the plate and the seats adapted to extend under the first side of the plate;
    b) a threaded bolt threadedly engaged within the threaded hole such that rotation of the bolt relative to the body causes the bolt to move into and out of the space such that movement of the bolt relative to the bracket can be effected to cause the bolt to contact the second side of the plate and clamp the plate between the bolt and the seats of the bracket; and
    c) a handle couplable relative to the bracket such that when a force is applied to the handle, the force is transferrable to the plate.

16. The bending tool according to claim 15, wherein:
    the handle is a bending iron having a shaft, a first end, and a second end angularly offset from both the shaft and first end, and the first and second ends include an opening that is sized and shaped to fit over a proximal end of the bracket and be rotationally fixed relative the bracket.

17. The bending tool according to claim 15, wherein:
the handle is flat and includes a first side and a second side, and the handle is reversible such that the distal end of the handle can be coupled to the bracket when either of the first or second sides of the handle faces the second side of the plate.

18. The bending tool according to claim 15, wherein:
the upper body of the bracket includes channels, and the distal end of the handle has an engagement portion that slides within the channels to rotationally fix the handle relative to the element.

19. The bending tool according to claim 18, wherein:
the channels are parallel, and the engagement portion includes two parallel sides surfaces that engage within the channels.

20. A set of bending tools for bending a bone plate, the bone plate having a first side, an opposite second side, and lateral sides extending between the first and second sides, the bone plate including a plurality of holes extending between the first and second sides, at least one of the set of bending tools comprising:
 a) a bracket having a pair of arms each including a seat at the end thereof, a space defined between the arms, the arms adapted to surround the lateral sides of the plate and the seats adapted to extend under the first side of the plate; and
 b) a handle movable relative to the bracket, the handle adapted to displace an end portion into direct contact with the plate to clamp the plate between the end portion and the seats of the bracket.

21. A set of bending tools for bending a bone plate, the bone plate having a lower side for placement on a bone, an opposite upper side, and lateral sides extending between the lower and upper sides, the bone plate including a plurality of holes extending between the upper and lower sides, at least one of the set of bending tools comprising:
 a) a bracket having arms including seats at the end thereof, a space defined between the arms, the arms adapted to surround the lateral sides of the plate and the seats adapted to extend under the lower side of the plate; and
 b) a handle movable relative to the bracket to contact the upper side of the plate and clamp the plate between a portion of the handle and the seats of the bracket.

* * * * *